United States Patent
Takemoto

(10) Patent No.: US 9,993,212 B2
(45) Date of Patent: Jun. 12, 2018

(54) X-RAY PHOTOGRAPHY DEVICE

(71) Applicant: THE YOSHIDA DENTAL MFG. CO., LTD., Tokyo (JP)

(72) Inventor: Terumi Takemoto, Tokyo (JP)

(73) Assignee: THE YOSHIDA DENTAL MFG. CO., LTD., Tokyo (JP)

( * ) Notice: Subject to any disclaimer, the term of this patent is extended or adjusted under 35 U.S.C. 154(b) by 177 days.

(21) Appl. No.: 15/118,962

(22) PCT Filed: Dec. 17, 2014

(86) PCT No.: PCT/JP2014/083338
§ 371 (c)(1),
(2) Date: Aug. 15, 2016

(87) PCT Pub. No.: WO2015/125393
PCT Pub. Date: Aug. 27, 2015

(65) Prior Publication Data
US 2017/0042490 A1 Feb. 16, 2017

(30) Foreign Application Priority Data
Feb. 24, 2014 (JP) .................. 2014-032480

(51) Int. Cl.
*A61B 6/03* (2006.01)
*A61B 6/14* (2006.01)
(Continued)

(52) U.S. Cl.
CPC .............. *A61B 6/032* (2013.01); *A61B 6/027* (2013.01); *A61B 6/14* (2013.01); *A61B 6/4452* (2013.01); *A61B 6/5205* (2013.01); *A61B 6/4441* (2013.01)

(58) Field of Classification Search
None
See application file for complete search history.

(56) References Cited

U.S. PATENT DOCUMENTS 8,837,668 B2 * 9/2014 Vartiainen ............... A61B 6/04
378/39
2011/0176717 A1 7/2011 Siren et al.
2012/0093284 A1 * 4/2012 Takemoto ............... A61B 6/02
378/19

FOREIGN PATENT DOCUMENTS

EP 2446822 A1 5/2012
JP 10-225455 A 8/1998
(Continued)

OTHER PUBLICATIONS

Oct. 2, 2017 Extended Search Report issued in European Patent Application No. 14883000.3.
(Continued)

*Primary Examiner* — Hoon Song
(74) *Attorney, Agent, or Firm* — Squire Patton Boggs (US) LLP

(57) ABSTRACT

A cross section obtained by cutting an X-ray beam at a time of taking projection data from the X-ray beam detected by an X-ray sensor, with a plane, which is perpendicular to the central axis of the X-ray beam and runs through the central axis of a photographic region, is defined as a photography specification surface. The number of the photography specification surface per unit area in a plane, as the photographic region is viewed from a point in the direction along the central axis of the photographic region, is defined as overlap density of the projection data. A controller of an X-ray photography device executes a leveling control which levels the overlap density of the projection data between at an outer portion and inner portion of the photographic region. Thus, an X-ray photographic device is provided that is capable of improving the image quality in the entire photographic region.

8 Claims, 18 Drawing Sheets

(51) Int. Cl.
    *A61B 6/02*    (2006.01)
    *A61B 6/00*    (2006.01)

(56)         References Cited

FOREIGN PATENT DOCUMENTS

JP           10-295680 A      11/1998
JP          2013-135842 A      7/2013
WO          2010037911 A1      4/2010
WO       WO 2014/069186 A1     5/2014

OTHER PUBLICATIONS

International Search Report & Written Opinion dated Feb. 10, 2015 corresponding to International Patent Application No. PCT/JP2014/083338 and English translation thereof.

* cited by examiner

X-RAY PHOTOGRAPHY DEVICE

CROSS-REFERENCE TO RELATED APPLICATION

This application is a U.S. National Stage Application under 35 U.S.C. § 371 of International Patent Application No. PCT/JP2014/083338 filed 17 Dec. 2014, which claims the benefit of priority to Japanese Patent Application No. 2014-032480 filed 24 Feb. 2014, the disclosures of all of which are hereby incorporated by reference in their entireties.

TECHNICAL FIELD

The invention relates to an X-ray photography device, particularly to an X-ray photography device for obtaining a computed tomography (CT) image.

BACKGROUND ART

An X-ray photography device for dental practice is known that includes: an X-ray source for irradiating an object with an X-ray beam; an X-ray imaging unit for detecting the X-ray beam transmitted through the object; and a swing drive unit for swinging the X-ray source and the X-ray imaging unit around the object, and is capable of taking a CT photograph and a panoramic photograph (see Japanese Patent Application Publication No. H10-225455). An X-ray photography device described in Japanese Patent Application Publication No. H10-225455 uses a two-dimensional sensor, having a wide detection area as required for taking a CT photograph, as an X-ray imaging unit.

SUMMARY OF THE INVENTION

Problems to be Solved

The X-ray photography device described in Japanese Patent Application Publication No. H10-225455 irradiates the whole of the object with an X-ray beam, while swinging the two-dimensional sensor having a wide detection area around the object, to take a photograph at a predetermined sampling time interval, more specifically, to obtain projection data from the X-ray beam detected by the two-dimensional sensor. In this case, overlap density of the projection data is different in the circumferential direction of the photographic region between an outer portion and inner portion of the photographic region having a cylindrical shape. That is, the overlap density of the projection data is rougher in the outer portion of the photographic region than that in the inner portion, to cause the image quality of the outer portion of the photographic region to be decreased from that of the inner portion.

The invention has been made in view of the above circumstances to provide an X-ray photography device that is capable of improving the image quality in the entire photographic region.

Solution to Problem

To solve the above problem, an X-ray photography device according to embodiments of the invention includes: an X-ray source that irradiates an object with an X-ray beam; an X-ray imager that detects the X-ray beam transmitted through the object; a support member that supports the X-ray source and the X-ray imager; a swing driver that rotates the support member to swing the X-ray source and the X-ray imager around the object; a shifter that shifts a portion of the object through which the X-ray beam to be detected by the imager is transmitted; and a controller that controls operation of the swing driver and the shifter, wherein assuming that a cross section obtained by cutting the X-ray beam at a time of taking projection data from the X-ray beam detected by the X-ray imager, with a plane, which is perpendicular to the central axis of the X-ray beam and runs through the central axis of a photographic region, is defined as a photography specification surface and the number of the photography specification surface per unit area in a plane, as the photographic region is viewed from a point in the direction along the central axis of the photographic region, is defined as overlap density of the projection data, the controller executes a leveling control which levels the overlap density of the projection data between at an outer portion and inner portion of the photographic region.

According to this configuration, the shifter can shift a portion of the object through which the X-ray beams to be detected by the X-ray imager is transmitted, to allow the X-ray imager having a relatively narrow detection area to function as a virtual wide-range two-dimensional X-ray imager that can cover a range corresponding to the shift of the transmitting portion, as well as to cause the overlap density of the projection data, at a time of the X-ray beam to be detected by the X-ray imager being transmitted through the outer portion of the photographic region, to be leveled with the overlap density of the projection data, at a time of the X-ray beam to be detected by the X-ray imager being transmitted through the inner portion of the photographic region.

Therefore, an X-ray photographic device can be provided that is capable of improving the image quality in the entire photographic region.

In other embodiments, the invention provides an X-ray photographic device, wherein the controller operates the swing driver for rotating the support member to swing the X-ray source and the X-ray imager around the object, and at the same time operates the shifter to shift a portion of the object through which the X-ray beam to be detected by the X-ray imager is transmitted, to make the X-ray imager detect the X-ray beam transmitted through the object.

According to such a configuration, the X-ray beam transmitted through the object can be detected, while the X-ray source and the X-ray imager are swung around the object and at the same time the portion of the object is shifted through which the X-ray beam to be detected by the X-ray imager is transmitted, to allow for reducing a halt and restart of a driven member such as the X-ray imager. As a result, a speed reduction due to the halt and restart of the driven member can be avoided from the beginning of the X-ray photography to the end thereof to allow for shortening an overall photographic time and for improving photographic efficiency. In addition, acceleration and deceleration acting on the driven member can be reduced to cause an inertial force due to the acceleration and deceleration to be reduced, allowing for reducing vibration of the driven member due to the inertial force to improve durability of the driven member. That is, an X-ray imager having a relatively narrow-range detection area can be used to reduce the cost, and also photographic efficiency can be improved as well as vibration of the driven member such as an X-ray imager can be reduced.

In other embodiments, the invention provides an X-ray photography device, wherein the leveling control makes a speed of shifting by the shifter a portion of the object through which the X-ray beam is transmitted at a time of the X-ray beam to be detected by the X-ray imager being transmitted through the outer portion of the photographic region, slower than a speed of shifting by the shifter the portion of the object through which the X-ray beam is transmitted at a time of the X-ray beam to be detected by the X-ray imager being transmitted through the inner portion of the photographic region.

According to such a configuration, the speed of shifting by the shifter a portion of the object through which the X-ray beam is transmitted can be varied between the outer and inner portions of the photographic region to allow for leveling the overlap density of the projection data at the outer and inner portions of the photographic region.

In other embodiments, the invention provides an X-ray photography device, wherein the leveling control makes the number of times for taking the projection data per unit time at a time of the X-ray beam to be detected by the X-ray imager being transmitted through the outer portion of the photographic region, larger than the number of times for taking the projection data per unit time at a time of the X-ray beam to be detected by the X-ray imager being transmitted through the inner portion of the photographic region.

According to such a configuration, the number of times for taking the projection data per unit time can be varied between the outer and inner portions of the photographic region to level the overlap density of the projection data at the outer and inner portions of the photographic region.

In other embodiments, the invention provides an X-ray photography device, wherein the leveling control makes a speed of swinging by the swing driver the X-ray source and the X-ray imager around the object at a time of the X-ray beam to be detected by the X-ray imager being transmitted through the outer portion of the photographic region, slower than a speed of swinging by the swing driver the X-ray source and the X-ray imager around the object at a time of the X-ray beam to be detected by the X-ray imager being transmitted through the inner portion of the photographic region.

According to such a configuration, the speed of swinging by the swing driver the X-ray source and the X-ray imager around the object can be varied between the outer and inner portions of the photographic region to level the overlap density of the projection data at the outer and inner portions of the photographic region.

Advantageous Effects of the Invention

According to the invention, an X-ray photography device is provided that is capable of improving the image quality in the entire photographic region.

DETAILED DESCRIPTION OF EMBODIMENTS

Figure 1:
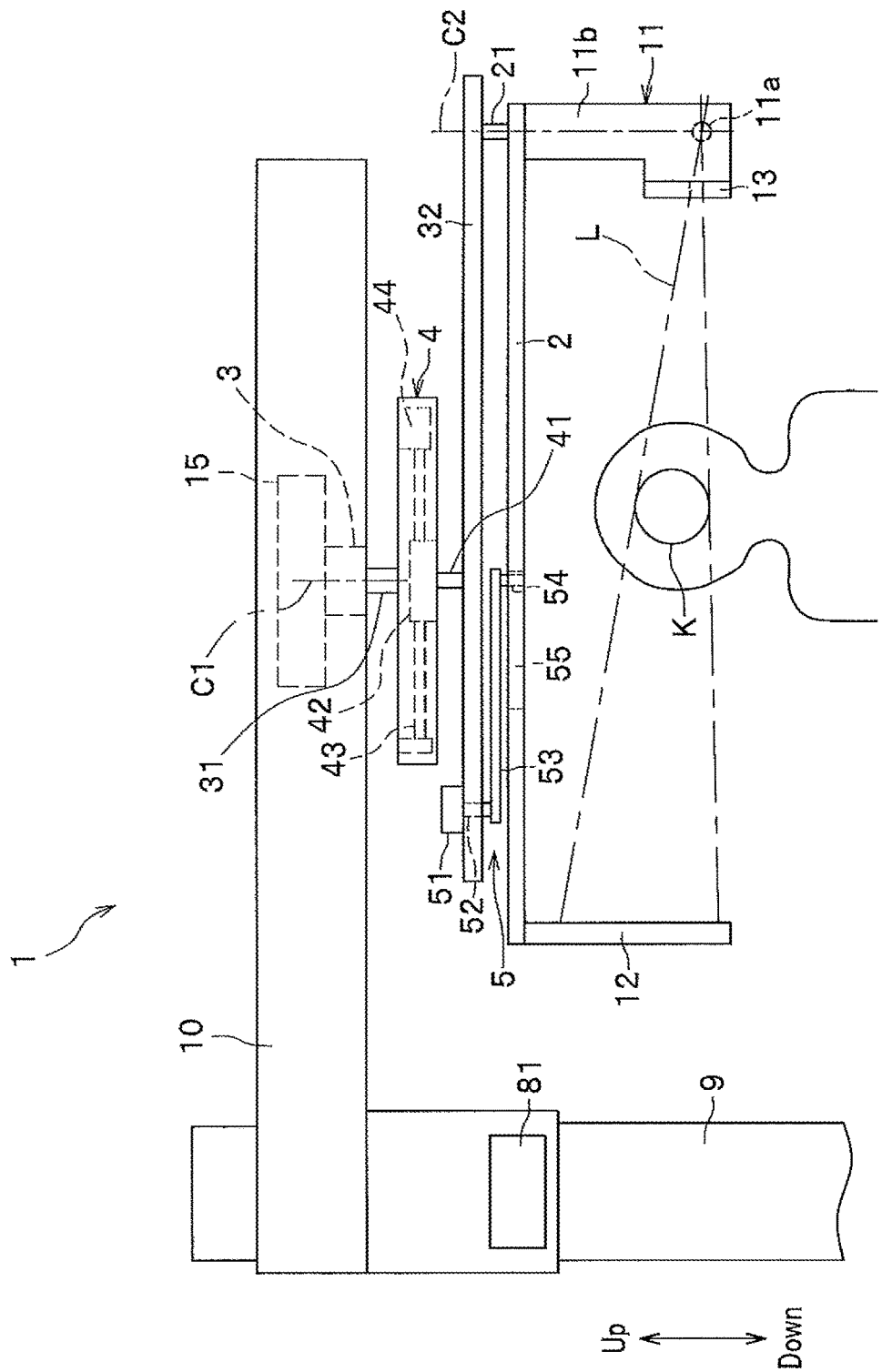
FIG. 1 is a side view schematically showing an overall configuration of an X-ray photography device according to a first embodiment of the invention.

A description will be given in detail of embodiments according to the invention with reference to the accompanying drawings.

Note that in the drawings described hereinafter, the same members or corresponding members will be denoted by the same reference numerals. In addition, dimensions and shapes of the members may be deformed or exaggerated for convenience of illustration in some cases to schematically show them.

First Embodiment

Figure 2:
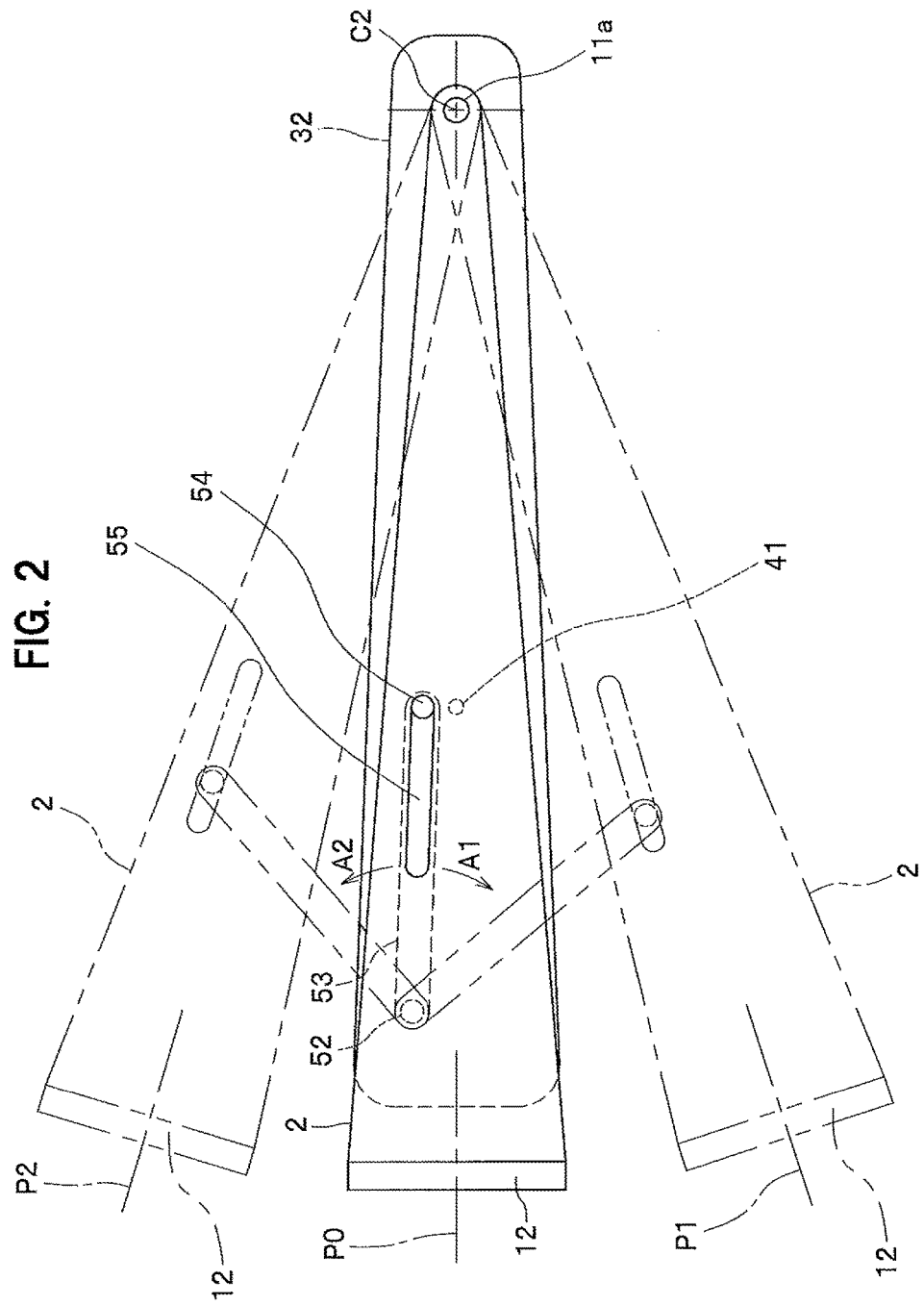
FIG. 2 is a bottom plan view of main portions for illustrating the operation of the shifter.

FIG. 1 is a side view schematically showing an overall configuration of an X-ray photography device 1 according to a first embodiment of the invention. FIG. 2 is a bottom plan view of main portions for illustrating the operation of a shifter 5.

As shown in FIG. 1, the X-ray photography device 1 for use in dentistry according to the first embodiment of the invention includes: a head 11 having an X-ray source 11*a* that irradiates an object K with an X-ray beam L; an X-ray sensor 12 as an X-ray imager; an arc motion arm 2 as a support member that supports the X-ray source 11*a* and the X-ray sensor 12; a swing driver 3 inclusive of a servo motor that rotates the arc motion arm 2 about an arm swing central-axis C1; and a shifter 5 that shifts a portion of the object K through which the X-ray beam L to be detected by the X-ray sensor 12 is transmitted.

Note that a description will be given in the present embodiment of a case where the device is applied to dentistry, however, it is not limited thereto and can be widely applied to a medical field and the like.

The swing driver 3 is installed on an XY table 15 and is configured to rotatably drive a swing shaft 31 via a deceleration mechanism (not shown). The XY table 15 allows the swing driver 3 and the swing shaft 31 to be movable in a two-dimensional plane.

The swing driver 3 and the XY table 15 are arranged in a frame 10 that extends in the horizontal direction, and is supported so as to be movable in the vertical direction relative to a strut 9 that extends in the vertical direction. Note that a reference numeral 81 in FIG. 1 shows an operation panel operated by an operator.

The swing shaft 31 is fixed to an upper portion of a horizontally-moving-swing-center-position mechanism 4 that includes a connecting shaft 41 which is fixed to the upper surface of a swing arm 32.

The horizontally-moving-swing-center-position mechanism 4 has a function of horizontally moving the connecting shaft 41 in the direction along the line connecting the X-ray source ha with the X-ray sensor 12, in particular, in the longitudinal direction of the swing arm 32. Here, the horizontally-moving-swing-center-position mechanism 4 includes: a nut portion 42 to which the connecting shaft 41 is fixed; a male screw member 43 that is screwed into the nut portion 42; and a male-screw-member rotation driver 44 such as a servo motor that rotates the male screw member 43. That is, with the male-screw-member rotation driver 44 in operation to rotate the nut portion 42, the horizontally-moving-swing-center-position mechanism 4 can shift, through a screw feed action, the connecting shaft 41 in a longitudinal direction of the swing arm 32 relative to the arm swing central-axis C1. According to such a configuration, the distance between the X-ray source 11*a* and the object K can be varied to allow for adjusting the size of a photographic region (field of view, or FOV) PA (see FIG. 12).

The swing driver 3 has a function of rotating the arc motion arm 2 via the horizontally-moving-swing-center-position mechanism 4 and the swing arm 32 to swing the X-ray source 11*a* and the X-ray sensor 12 around the object K.

The shifter 5 has a function of shifting a portion of the object K, through which the X-ray beam to be detected by the X-ray sensor 12 is transmitted, in a direction substantially perpendicular to a line connecting the X-ray source 11*a* with the X-ray sensor 12. In the present embodiment, the shifter 5 is an arc motion driver that causes the X-ray sensor 12 to be rotated about an arc motion central-axis C2 arranged on a line connecting the object K with the X-ray sensor 12 so as to be moved in an arc around the object K.

With such a configuration, the X-ray photography device 1 can swing the swing arm 32 by the swing driver 3 to rotate the arc motion arm 2 for rotating the X-ray source 11*a* and the X-ray sensor 12 around the object K, and rotate the arc motion arm 2 by the shifter 5 to make the X-ray sensor 12 move in an arc across the object K.

The X-ray source 11*a* is arranged in a support portion 11*b* which is fixed downward to the arc motion arm 2. Accordingly, the irradiation direction of the X-ray beam L radiated from the X-ray source 11*a* varies with the rotation of the arc motion arm 2, and the X-ray sensor 12 also moves in an arc while synchronously following the radiation direction of the X-ray beam L (see FIG. 2).

In addition, a slit 13 for restricting the range of the X-ray beam L radiated from the X-ray source 11*a* is arranged on a surface facing the object K of the head 11 so as to face the X-ray sensor 12 across the object K. The slit 13 causes the X-ray beam L to be focused on the object K and then to be transmitted through the object K so as to be detected by the X-ray sensor 12. Arranging the slit 13 allows for reducing the amount of scattered radiation to improve image quality. Note that the slit 13 may be arranged so as to droop from the arc motion arm 2.

The X-ray sensor 12 detects the X-ray beam L which is transmitted through the object K, and can be configured to use an image sensor having a relatively-narrow-range and vertically-long detection area such as a CMOS sensor, a CCD sensor, or a CdTe sensor.

For example, the CMOS sensor has characteristics of having a low cost and using less power, while the CCD sensor has characteristics of having high resolution, to allow for selecting a suitable image sensor on the basis of the required specifications of the X-ray photography device.

The arc motion arm 2 is rotatably supported about a shaft member 21 having the arc motion central-axis C2, which is arranged to the swing arm 32 that is swung by the swing driver 3. The arc motion central-axis C2 is here arranged coaxially with the X-ray source 11*a* in the head 11 arranged to the arc motion arm 2. With this structure, the X-ray sensor 12 is made to move in an arc about the X-ray source 11*a*, without the X-ray source 11*a* being moved in an arc, to allow for radiating a stable X-ray beam L to reduce blurring of the image. In addition, if the X-ray source 11*a* is rotated in the moving direction of the X-ray sensor 12 in accordance with the arc motion of the X-ray sensor 12, for example, a certain range of the X-ray beam can be radiated to the X-ray imager to allow for irradiating the object K always with the uniform X-ray beam L having no unevenness.

The arc motion arm 2 has the X-ray source 11*a*, the slit 13, and the X-ray sensor 12 arranged in a straight line. Accordingly, a certain range of the X-ray beam L radiated from the X-ray source 11*a* can be focused by the slit 13 before being radiated toward the X-ray sensor 12, allowing for efficiently irradiating the object K always with the uniform X-ray beam L having no unevenness.

As shown in FIGS. 1 and 2, the shifter 5 is configured to include: a pivot arm driver 51 such as a servo motor that is installed on the swing arm 32; a rotary shaft 52 that is connected to the pivot arm driver 51; a pivot arm 53 that has a tip of the rotary shaft 52 fixed at one end; a drive pin 54 that is arranged at the other end of the pivot arm 53; and a guide groove 55 that is formed on the arc motion arm 2 so as to be engaged with the drive pin 54.

With such a configuration, the shifter 5 makes the arc motion arm 2 move in an arc about the arc motion central-axis C2 from a center position P0 to an angled position P1 in FIG. 2, on the condition that the pivot arm 53 is rotated about the rotary shaft 52 in the clockwise direction A1 in FIG. 2, and likewise makes the arc motion arm 2 move in an arc about the arc motion central-axis C2 from the center position P0 to an angled position P2 in FIG. 2, on the condition that the pivot arm 53 is rotated about the rotary shaft 52 in the counterclockwise direction A2 in FIG. 2.

In this way, the arc motion arm 2 is driven to move in an arc about the arc motion central-axis C2 so that the slit 13 and the X-ray sensor 12 arranged with the arc motion arm 2 can move in an arc.

The XY table 15, even though it is not shown, is formed by combining a linearly moving guide, which is arranged so as to be movable in the X-axis direction, and a linearly moving guide, which is arranged so as to be movable in the Y-axis direction, that are arranged so as to be orthogonal in the horizontal direction.

With the XY table 15, the X-ray photography device 1 can horizontally translate the arc motion arm 2 in the two-dimensional plane, to function as a photography device which can take both a CT image and a panoramic image.

That is, the X-ray photography device 1 can be used as a CT photography device to take CT photography by locking the XY table 15 for fixing a position in the horizontal plane of the arm swing central-axis C1. On the other hand, the X-ray photography device 1 can be used as a conventional panoramic photography device to take panoramic photography by the XY table 15 horizontally and integrally translating the arc motion arm 2 and the swing arm 32 in the two-dimensional plane, in a state that the arc motion arm 2 is locked to have no arc motion.

Figure 3:
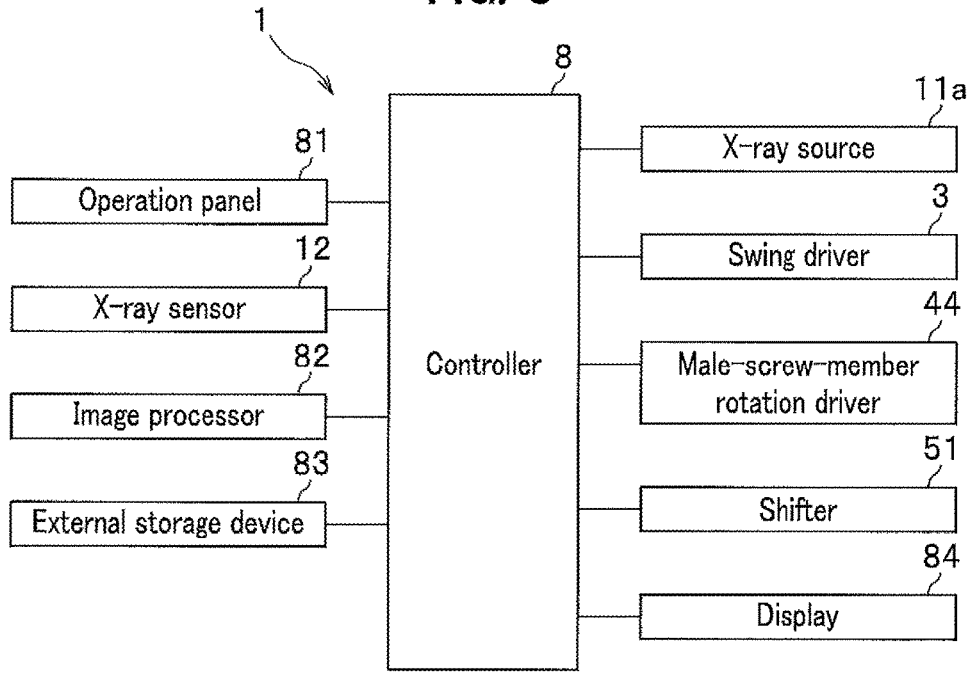
FIG. 3 is a block diagram showing a main configuration for controlling an X-ray photography device.

FIG. 3 is a block diagram showing a main configuration for controlling the X-ray photography device 1.

As shown in FIG. 3, the X-ray photography device 1 includes a controller 8 that executes overall control of the entire X-ray photography device 1. For example, the controller 8 controls the X-ray photography of the object K. That is, the controller 8 controls the X-ray source 11a radiating an X-ray beam, as well as the X-ray sensor 12 detecting the X-ray beam L that has transmitted through the object K (see FIG. 1). Additionally, the controller 8 controls the operation of the swing driver 3, the pivot arm driver 51 of the shifter 5 (see FIG. 1), and the male-screw-member rotation driver 44.

In the present embodiment, the controller 8 is configured to control the X-ray photography of the object K, while rendering the X-ray source 11a and the X-ray sensor 12 swung around the object K (see FIG. 1) along with a portion of the object K shifted through which the X-ray beam L (see FIG. 1) to be detected by the X-ray sensor 12 is transmitted.

In addition, the X-ray photography device 1 further includes an image processer 82, an external storage device 83, and a display 84, all of which are connected to the controller 8. The image processor 82 executes image processing on image data (projection data) obtained by the X-ray sensor 12 detecting the X-ray beam, to generate various images such as a CT image and a panoramic image. The external storage device 83 is a hard disk device or an optical disk device, for example, which can store various images. The display 84 is a liquid crystal display (LCD), for example, which can display various images.

Further, by way of the operation panel 81, various photography modes such as a CT photography mode and a panoramic radiography mode can be switched, or a shift amount can be set for shifting a portion of the object K through which the X-ray beam L to be detected by the X-ray sensor 12 is transmitted, for example.

Figure 4:
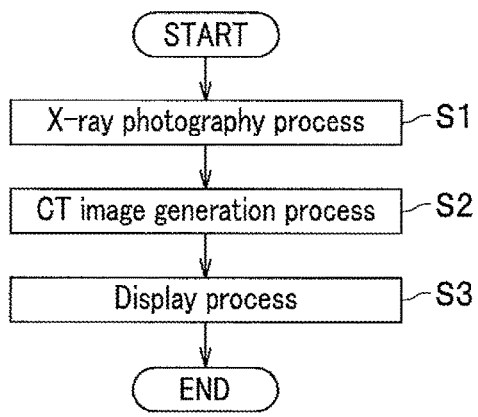
FIG. 4 is a flowchart showing an overall procedure of CT photography operation.

A description will be given of operation of the X-ray photography device 1 as configured above, with reference to FIGS. 4 to 11. FIG. 4 is a flowchart showing an overall procedure of CT photography operation. FIGS. 5 to 9 are plan views, each schematically showing each of a first to fifth rounds of swinging the X-ray source and the X-ray sensor around the object.

As shown in FIG. 4, by way of the operator operating the operation panel 81 (see FIGS. 1 and 3), an X-ray photography process is executed by the X-ray photography device 1 (step S1). Here, a description will be given of a case of executing CT photography.

In the present embodiment, while making the swing driver 3 (see FIG. 1) rotate the arc motion arm 2 to swing the X-ray source 11a and the X-ray sensor 12 around the object K along with making the shifter 5 (see FIG. 1) shift a portion of the object K through which the X-ray beam L to be detected by the X-ray sensor 12 is transmitted, the controller 8 (see FIG. 3) makes the X-ray sensor 12 detect the X-ray beam L which has transmitted the object K.

Note that a description will be given later about how to obtain the projection data from the X-ray beam L detected by the X-ray sensor 12.

Figure 5:
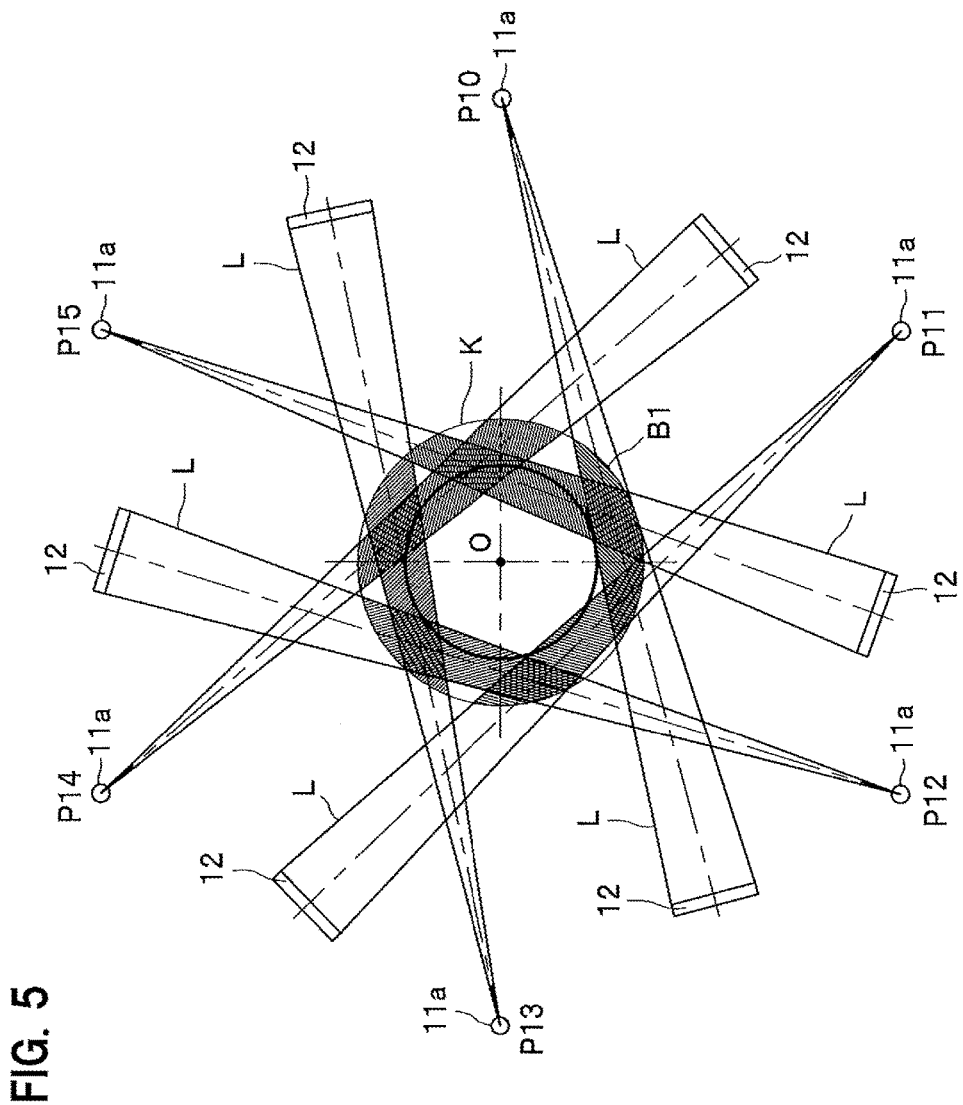
FIG. 5 is a plan view schematically showing a first round of swinging the X-ray source and the X-ray sensor around the object.

As shown in FIG. 5, the X-ray beam L radiated from the X-ray source 11a first at a position P10 (position of 0°) in FIG. 5 for the first round is transmitted through a first region B1 in FIG. 5 corresponding to the outermost (the lowest in FIG. 5) of the object K, and then detected by the X-ray sensor 12. In the first round, the X-ray source 11a and the X-ray sensor 12 are swung around the object K, so that the X-ray source 11a is rotated by 360° from this state through positions P11-P15 to a position P16 (see FIG. 6), and at the same time a portion of the object K through which the X-ray beam L to be detected by the X-ray sensor 12 is transmitted is gradually shifted upward from the first region B1 in FIG. 5 to a second region B2 in FIG. 6.

Figure 6:
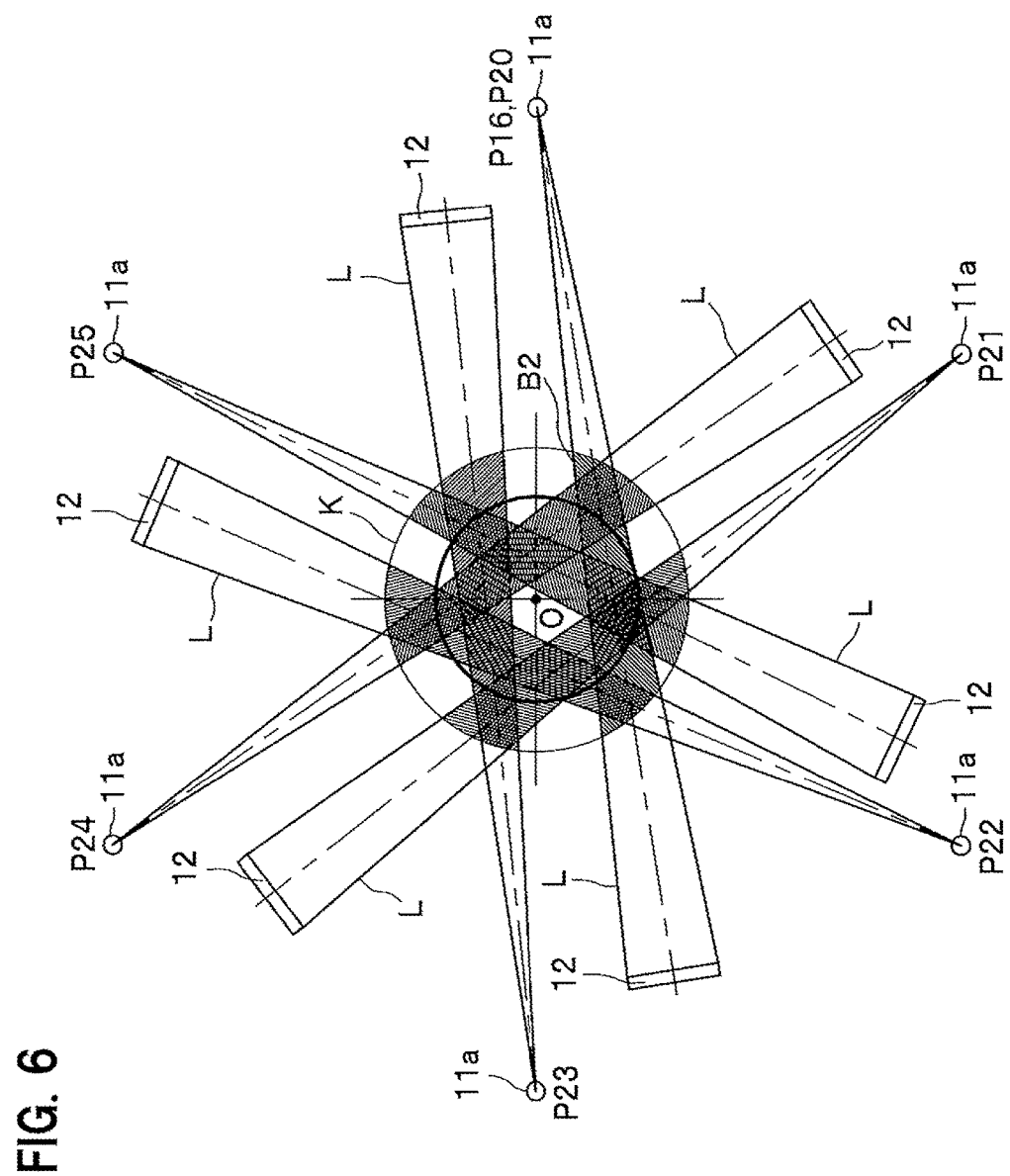
FIG. 6 is a plan view schematically showing a second round of swinging the X-ray source and the X-ray sensor around the object.
Figure 7:
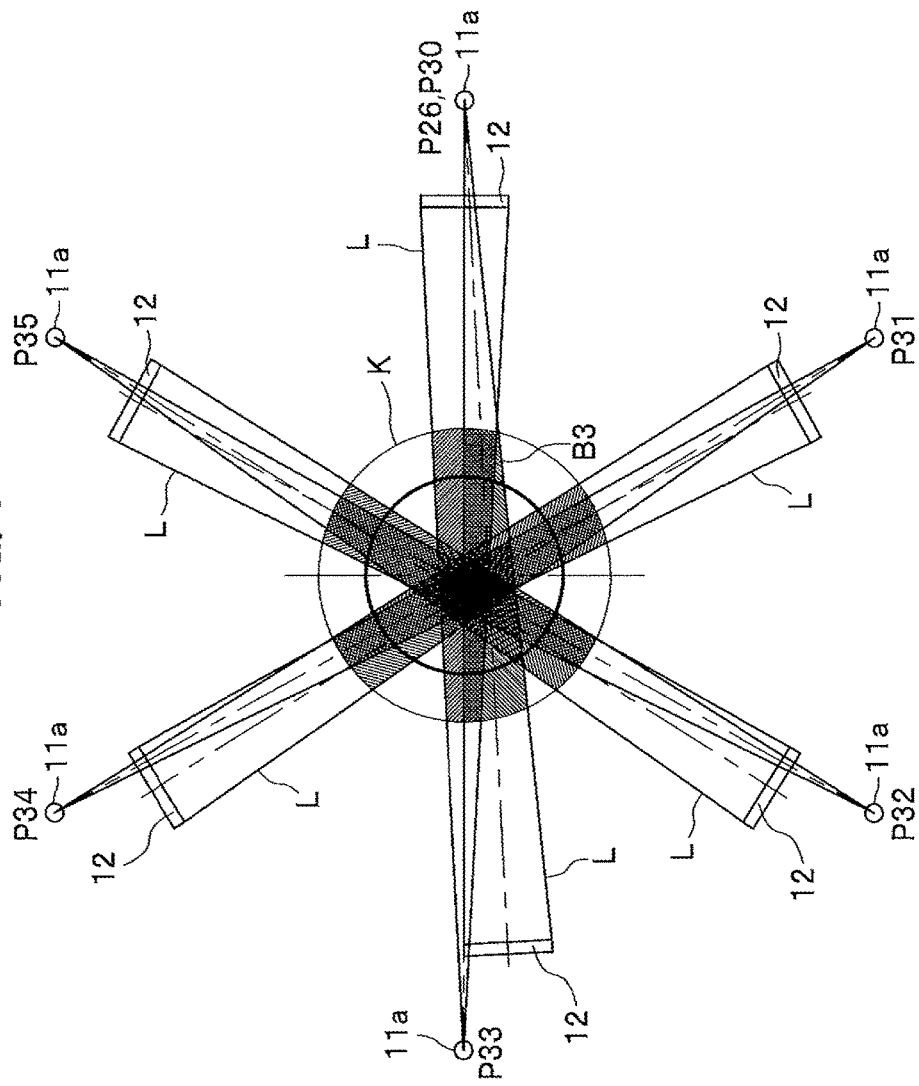
FIG. 7 is a plan view schematically showing a third round of swinging the X-ray source and the X-ray sensor around the object.
Figure 8:
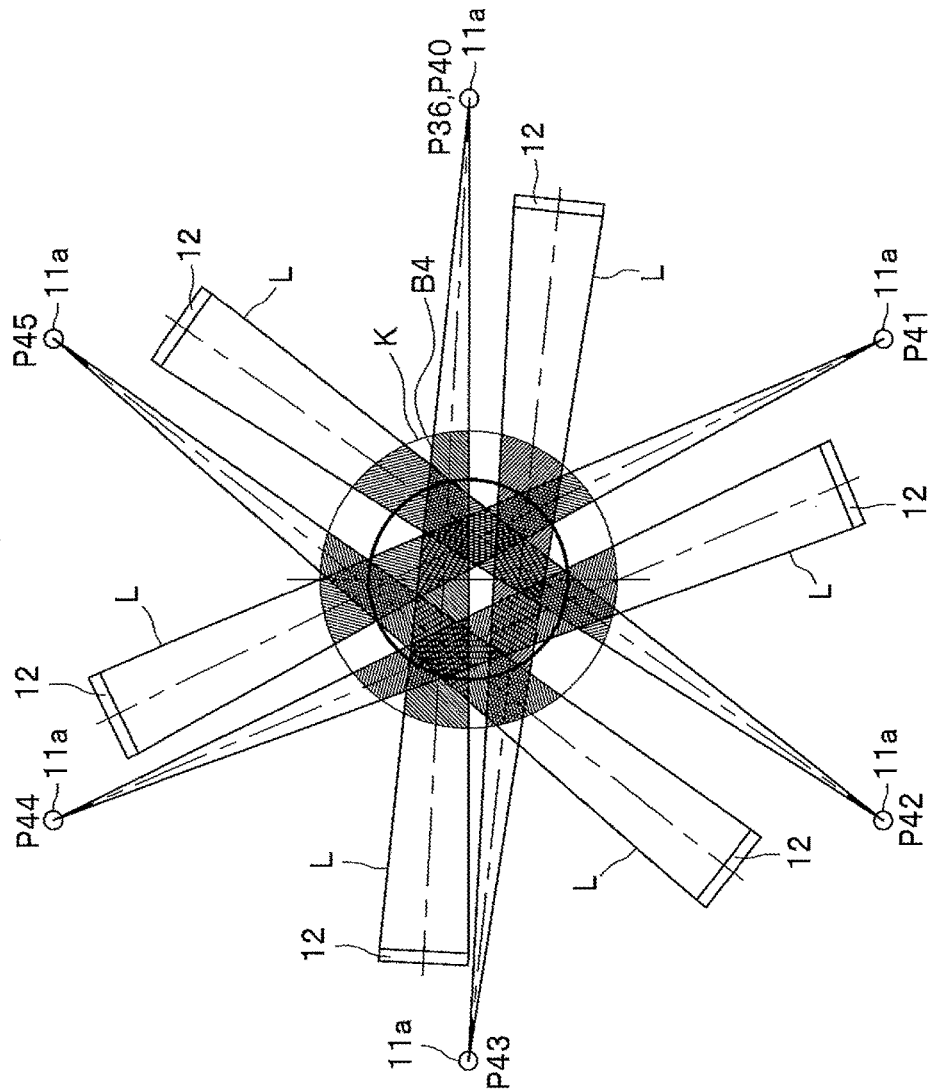
FIG. 8 is a plan view schematically showing a fourth round of swinging the X-ray source and the X-ray sensor around the object.
Figure 9:
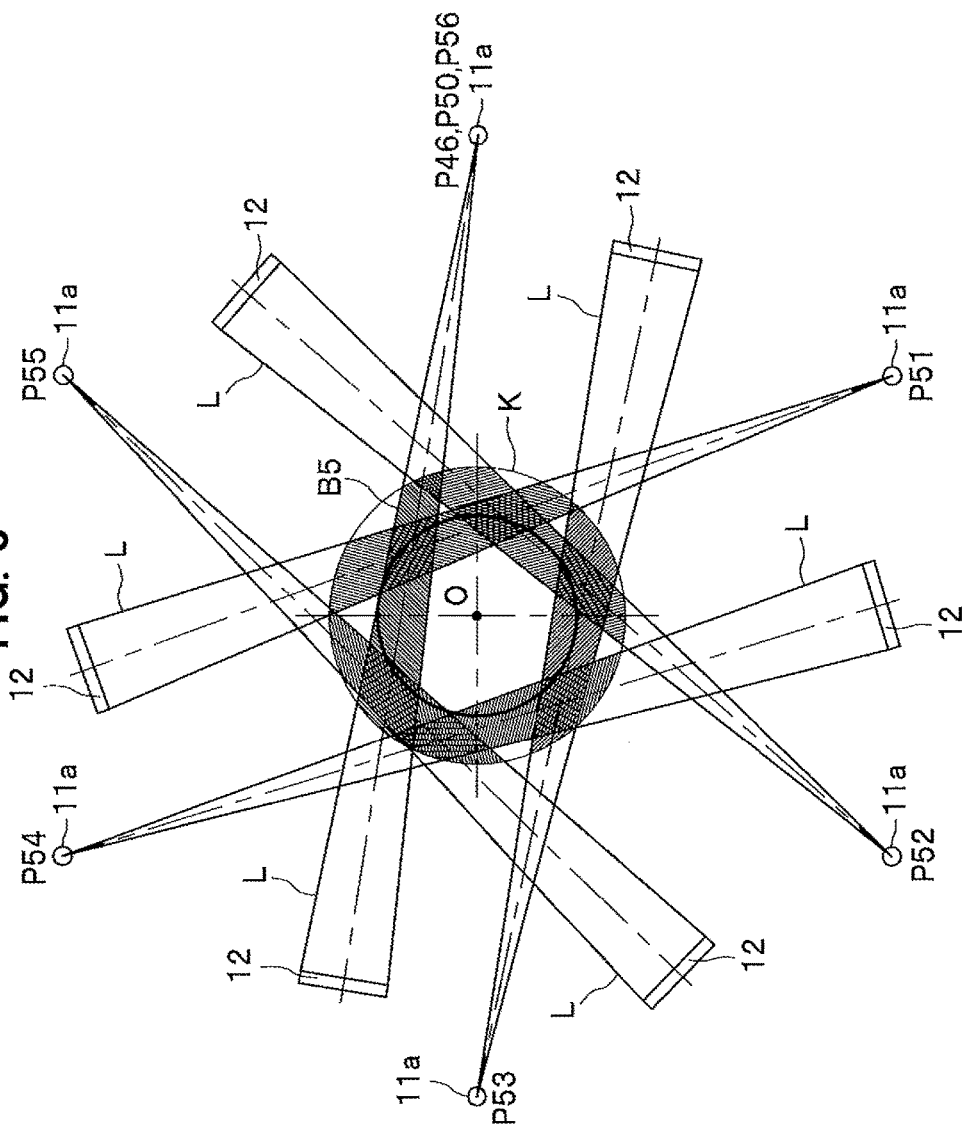
FIG. 9 is a plan view schematically showing a fifth round of swinging the X-ray source and the X-ray sensor around the object.

Similarly, in the second round, as shown in FIG. 6, the X-ray source 11a at a position P20 (position of 0°) in FIG. 6 is rotated by 360° through positions P21-P25 to a position P26 (see FIG. 7), and at the same time a portion of the object K through which the X-ray beam L to be detected by the X-ray sensor 12 is transmitted is gradually shifted upward from the second region B2 in FIG. 6 to a third region B3 in FIG. 7. In the third round, as shown in FIG. 7, the X-ray source 11a at a position P30 (position of 0°) in FIG. 7 is rotated by 360° through positions P31-P35 to a position P36 (see FIG. 8), and at the same time a portion of the object K through which the X-ray beam L to be detected by the X-ray sensor 12 is transmitted is gradually shifted upward from the third region B3 in FIG. 7 to a fourth region B4 in FIG. 8. In the fourth round, as shown in FIG. 8, the X-ray source 11a at a position P40 (position of 0°) in FIG. 8 is rotated by 360° through positions P41-P45 to a position P46 (see FIG. 9), and at the same time a portion of the object K through which the X-ray beam L to be detected by the X-ray sensor 12 is transmitted is gradually shifted upward from the fourth region B4 in FIG. 8 to a fifth region B5 in FIG. 9. Then, in the fifth round, as shown in FIG. 9, the X-ray source 11a at a position P50 (position of 0°) in FIG. 9 is rotated by 360° through positions P51-P55 to a position P56, and at the same time a portion of the object K through which the X-ray beam L to be detected by the sensor 12 is transmitted is gradually shifted upward from the fifth region B5 in FIG. 9. Note that in FIG. 9, a portion through which the X-ray beam is transmitted is not shown for the X-ray source 11a at the position P56.

Figure 10:
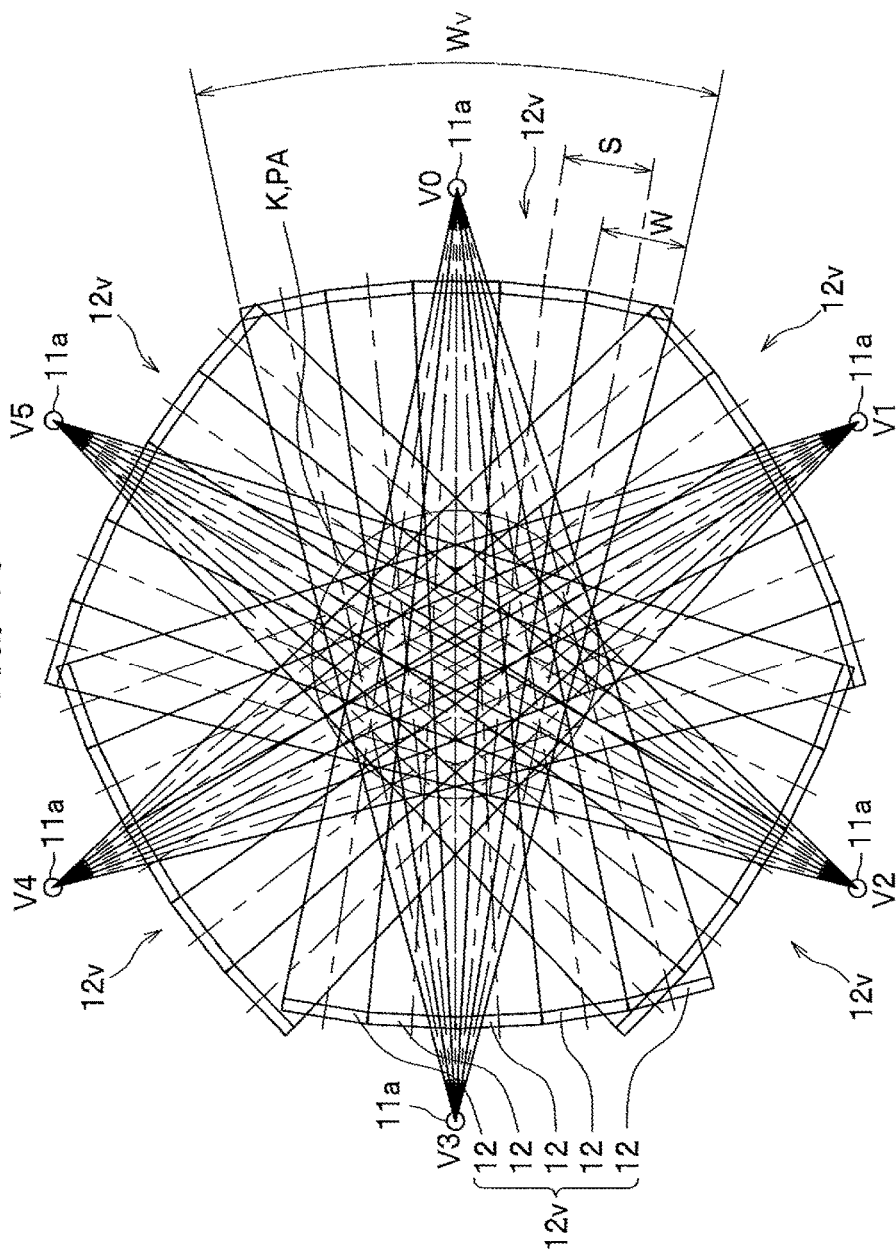
FIG. 10 is a plan view showing FIGS. 5 to 9 superimposed.
Figure 11:
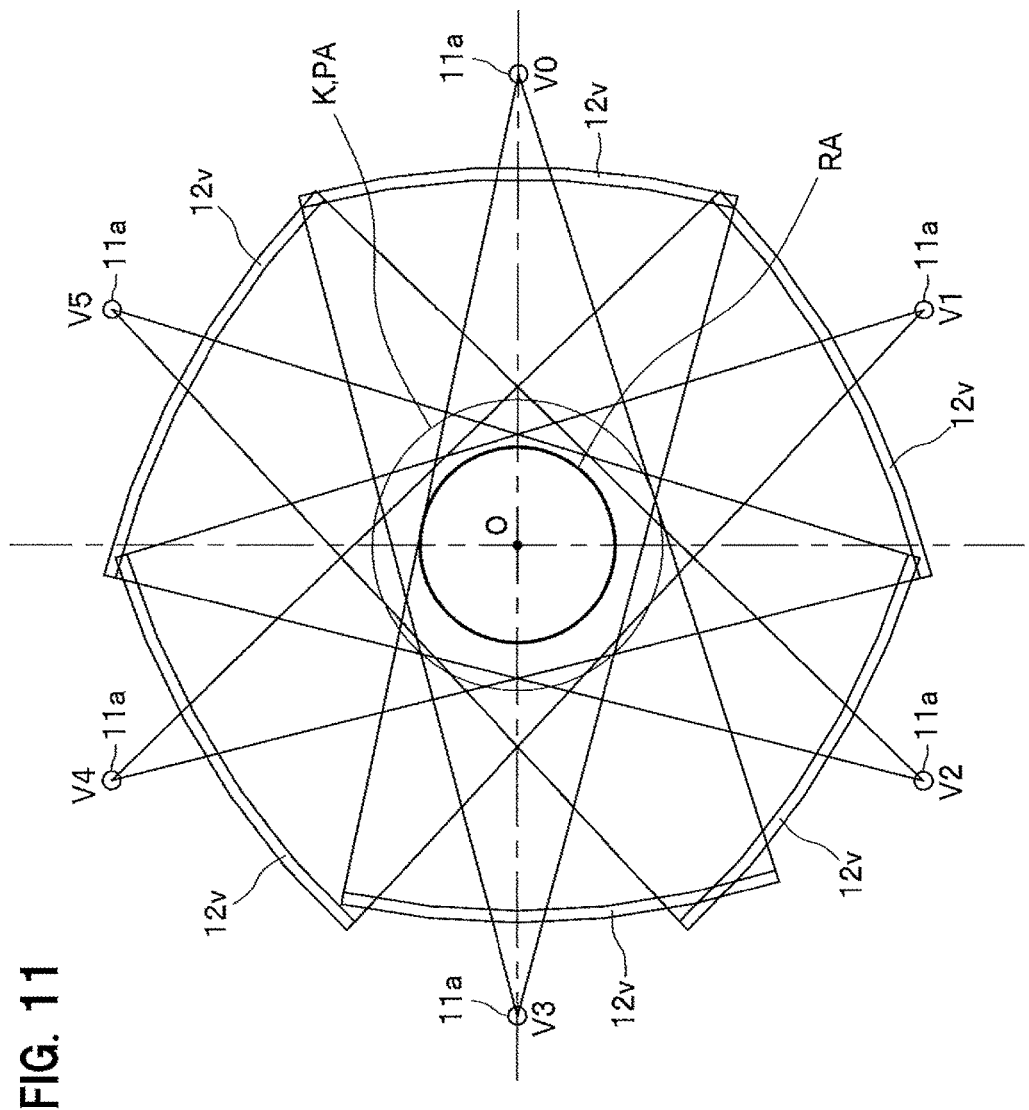
FIG. 11 is a plan view for illustrating a region where reconstructive image can be obtained.

FIG. 10 is a plan view showing FIGS. 5 to 9 superimposed. FIG. 11 is a plan view for illustrating a region where reconstructive image can be obtained.

As shown in FIG. 10, at the same angular positions (positions V0-V5) of respective rounds, the X-ray source 11a is located at the same positions, respectively, while the positions of the X-ray sensor 12 are moved in an arc about the position of the X-ray source 11a, that is, shifted as the round advances. In other words, FIG. 10 corresponds to a plan view schematically showing a case in which a wide-range virtual X-ray sensor 12v that is virtually formed by shifting the X-ray sensor 12 is swung one trip around the object K. In FIG. 10, a region of the object K indicates the photographic region PA.

In addition, in the present embodiment, the controller 8 controls operation of the swing driver 3 and the shifter 5 so that a portion through which the X-ray beam L has been transmitted before one rotation of the arc motion arm 2 via the swing arm 32, and a portion through which the X-ray beam L radiated from the same position of the rotation as above is transmitted after the one rotation and which is adjacent to the preceding portion, are in contact with each other. In this case, a shift amount S of the X-ray sensor 12 shifting while the arc motion arm 2 makes one rotation is substantially equal to the width of the X-ray sensor 12 (effective width) W. In the example of FIG. 10, it is enough to rotate the arc motion arm 2 by (a width Wv of the virtual X-ray sensor 12v)/(the width W of the X-ray sensor 12)=5 times, while shifting the X-ray sensor 12. According to such a configuration, the image data (projection data) required for generating a CT image can efficiently be obtained, allowing for further improving photography efficiency while securing the image quality.

Note that in the present embodiment, a portion of the object K through which the X-ray beam L to be detected by the X-ray sensor 12 is transmitted is shifted while the X-ray source 11a and the X-ray sensor 12 swing around the object K. Accordingly, in the example shown in FIG. 11, the image data (projection data) fails to be obtained from all directions for a region having the width of the X-ray sensor 12 at the outer periphery of the photographic region PA, and therefore it difficult to generate a reconstructive image such as a CT image for the region. Then, a reconstructive-image obtainable region RA (see FIG. 11) is a region that remains after removing the outer periphery of the photographic region PA by the width of the X-ray sensor 12.

Returning to step S2 in FIG. 4, once the image data (projection data) obtained by the CT photography is transferred to the image processer 82, the controller 8 controls the image processer 82 executing predetermined image processing on the image data (projection data) to generate a CT image.

Subsequently, the controller 8 displays the generated CT image on the display 84 (step S3). In addition, the generated CT image can be stored in the external storage device 83 as appropriate.

Next, a description will be given about how to obtain the projection data from the X-ray beam L detected by the X-ray sensor 12, with reference to FIGS. 12 to 14.

Figure 12:
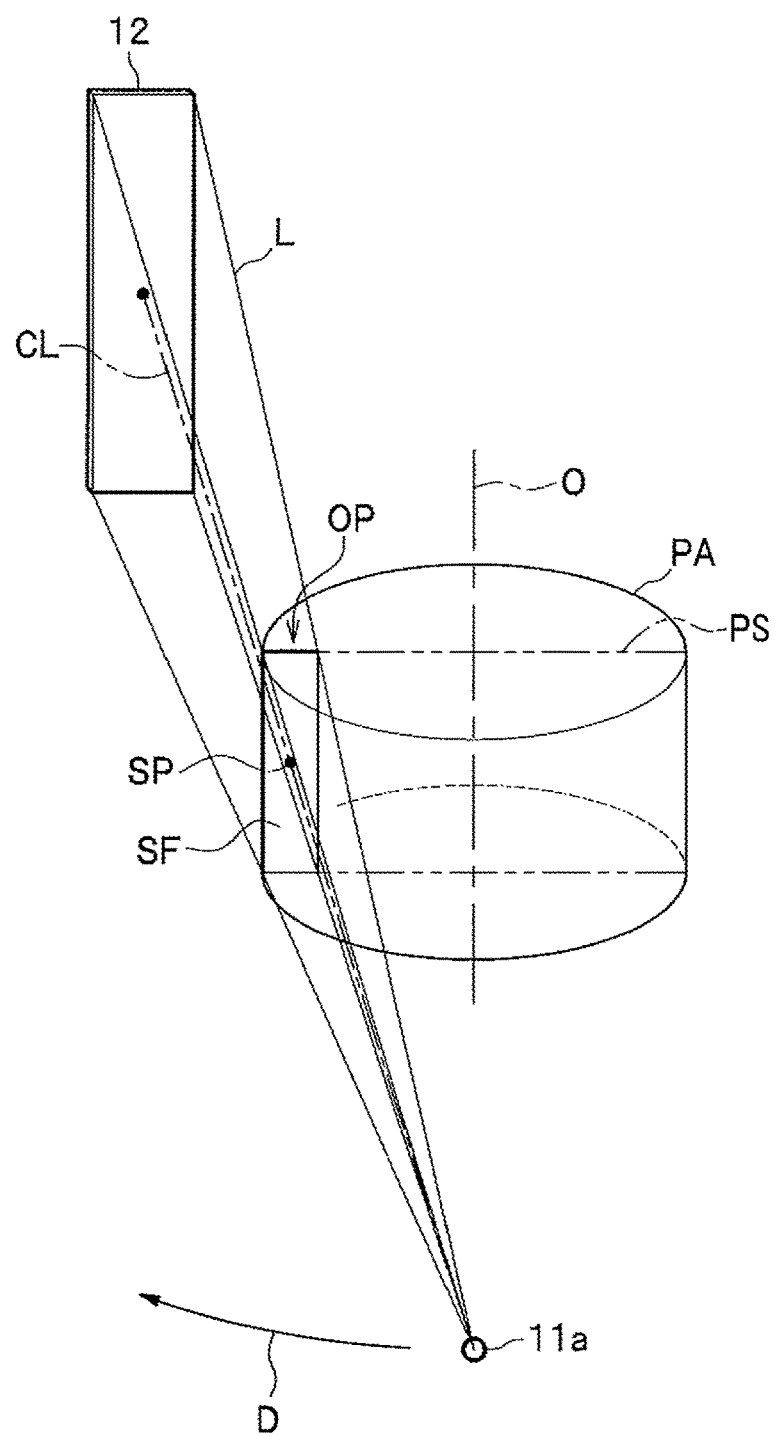
FIG. 12 is a perspective view schematically showing the X-ray beam to be detected by the X-ray sensor being transmitted through the outer portion of the photographic region.

FIG. 12 is a perspective view schematically showing the X-ray beam L to be detected by the X-ray sensor 12 being transmitted through the outer portion OP of the photographic region PA. FIG. 13 is a perspective view schematically showing the X-ray beam L to be detected by the X-ray sensor 12 being transmitted through the inner portion IP of the photographic region PA. FIG. 14 is a partial plan view schematically showing the photographic region PA as viewed from a point in the direction along the central axis O. Here, in the photographic region PA having a cylindrical shape, a portion far from the central axis O is referred to as the outer portion OP, and a portion closer to the central axis O than the outer portion OP is referred to as the inner portion IP. That is, the outer portion OP and inner portion IP are relatively defined in accordance with the distance from the central axis O.

Figure 13:
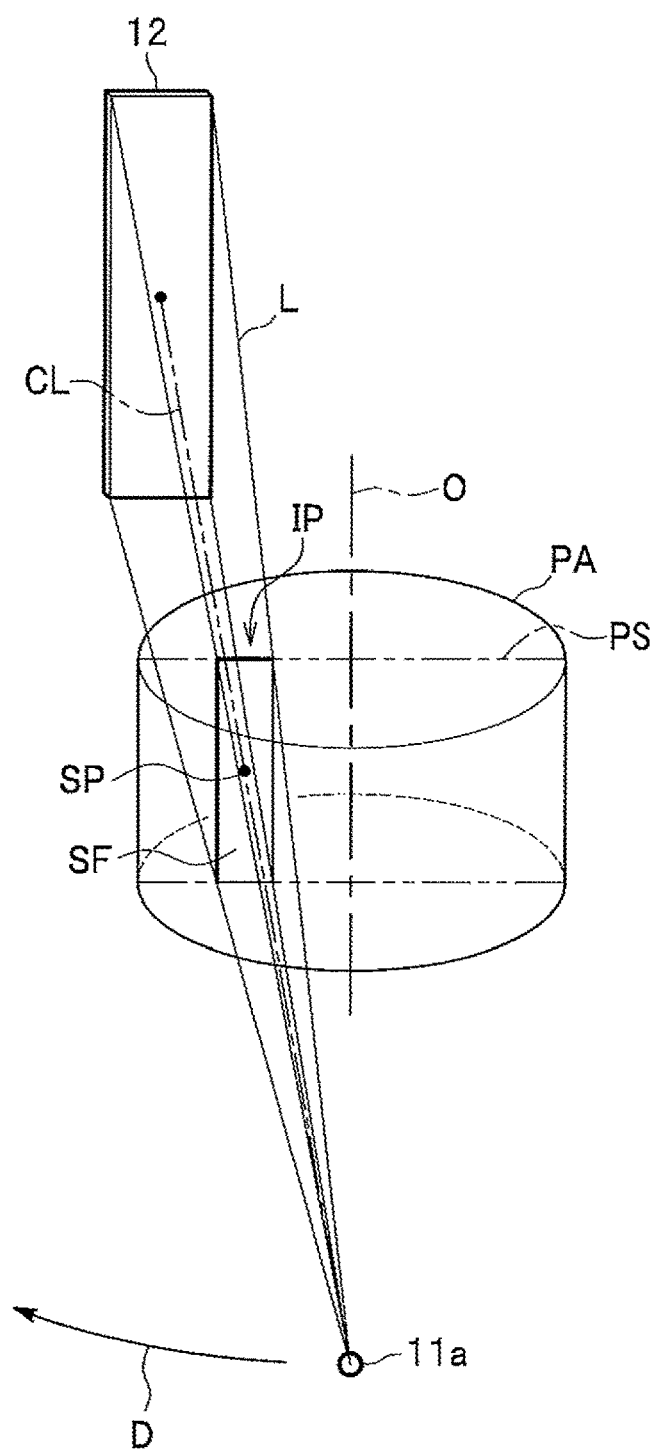
FIG. 13 is a perspective view schematically showing the X-ray beam to be detected by the X-ray sensor being transmitted through the inner portion of the photographic region.

As shown in FIGS. 12 and 13, a cross section obtained by cutting the X-ray beam L at a time of taking projection data from the X-ray beam L detected by the X-ray sensor 12, with a plane PS, which is perpendicular to the central axis CL of the X-ray beam L and runs through the central axis O of the photographic region PA, is defined as a photography specification surface SF. In addition, the number of the photography specification surfaces SF per unit area in a plane (see FIG. 14), as the photographic region PA is viewed from a point in the direction along the central axis O of the photographic region PA, is defined as overlap density of the projection data. That is, the overlap density of the projection data corresponds to the number of the photography specification surfaces SF (the number of overlapping sheets) per unit area in the plane (plane of paper) shown in FIG. 14.

Figure 14:
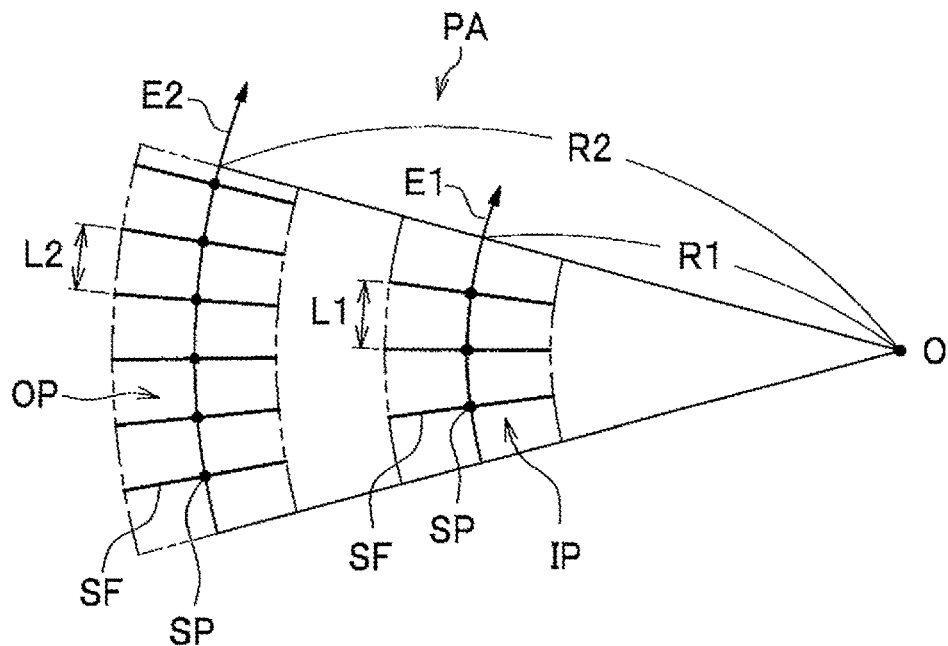
FIG. 14 is a partial plan view schematically showing the photographic region as viewed from a point in the direction along its central axis.

Note that a reference numeral SP in each of FIGS. 12 to 14 shows a photographic specification point which is an intersection between the central axis CL of the X-ray beam L and the photography specification surface SF. The photography specific surfaces SF and the photography specification points SP in FIG. 14 are smaller in number than in reality, for convenience of illustration (this also holds true in FIGS. 15 and 20 to be described later).

Then, the controller 8 executes a leveling control which levels the overlap density of the projection data at the outer portion OP and inner portion IP of the photographic region PA. The leveling control according to the present embodiment makes the number of times for taking the projection data per unit time at a time of the X-ray beam L to be detected by the X-ray sensor 12 being transmitted through the outer portion OP of the photographic region PA, larger than the number of times for taking the projection data per unit time at a time of the X-ray beam L to be detected by the X-ray sensor 12 being transmitted through the inner portion IP of the photographic region PA. Note that the number of times for taking the projection data per unit time is equivalent to the reciprocal of the sampling time interval of the projection data.

In the present embodiment, the speed of the swing driver 3 swinging in the direction D the X-ray source 11a and the X-ray sensor 12 around the object K is constant and assumed to have an angular velocity of $\omega$. As shown in FIG. 14, a circumferential speed E1 about the central axis O of the photography specification surface SF is calculated as $E1=R1*\omega$ at a time of the X-ray beam L to be detected by the X-ray sensor 12 being transmitted through the inner portion IP of the photographic region PA. Then, assuming that the sampling time interval for the projection data at the inner portion IP is T1, a circumferential distance L1 between the adjacent photography specification surfaces SF in the circumferential direction is calculated as $L1=E1*T1=R1*\omega*T1$. On the other hand, a circumferential speed E2 around central axis O of the photography specification surface SF is calculated as $E2=R2*\omega$ at a time of the X-ray beam L to be detected by the X-ray sensor 12 being transmitted through the outer portion OP of the photographic region PA. Then, assuming that the sampling time interval for the projection data at the outer portion OP is T2, a circumferential distance L2 between the adjacent photography specification surface SF in the circumferential direction is calculated as $L2=E2*T2=R2*\omega*T2$.

Therefore, the sampling time interval T2 for the projection data at the outer portion OP can be made shorter than the sampling time interval T1 for the projection data at the inner portion IP so as to be $T2=(R1/R2)*T1$, to make $L2=L1$.

Thus, the number of times for taking the projection data per unit time can be varied between the outer portion OP and inner portion IP of the photographic region PA to level the overlap density of the projection data at the outer portion OP and inner portion IP of the photographic region PA.

Figure 15:
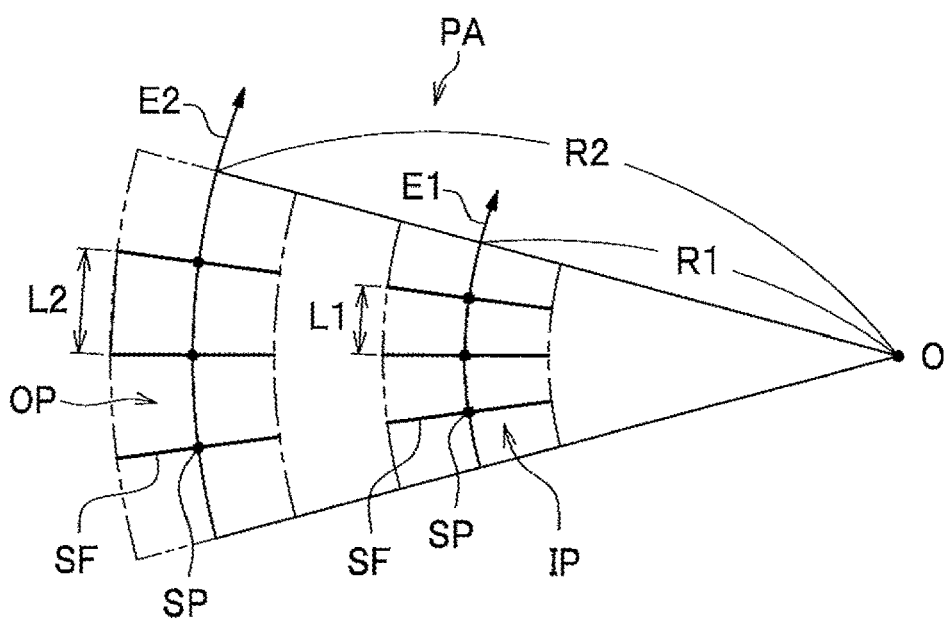
FIG. 15 is a partial plan view schematically showing a photographic region according to a comparative example, as viewed from a point in the direction along its central axis.

FIG. 15 is a partial plan view schematically showing the photographic region PA according to a comparative example, as viewed from a point in the direction along the central axis O of the photographic region PA. In this comparative example, the number of times for taking the projection data per unit time is the same between the condition that the X-ray beam L to be detected by the X-ray sensor 12 is transmitted through the outer portion OP of the photographic region PA and the condition that the beam is transmitted through the inner portion IP. In this comparative example, the sampling time interval T for the projection data is constant both at the outer portion OP and inner portion IP of the photographic region PA, to have a relationship of L2=R2*ω*T>R1*ω*T=L1. Accordingly, the overlap density of the projection data is rougher at the outer portion OP of the photographic region PA than at the inner portion IP, to cause the image quality of the outer portion OP of the photographic region PA to be lower than that of the inner portion IP.

As described above, according to the present embodiment, the shifter 5 can shift a portion of the object K through which the X-ray beam L to be detected by the X-ray sensor 12 is transmitted, to allow the X-ray sensor 12 having a relatively narrow-range detection area to function as a virtual wide-range two-dimensional X-ray imager that can cover a range corresponding to the shift of the portion, as well as to cause the overlap density of the projection data, at a time of the X-ray beam L to be detected by the X-ray sensor 12 being transmitted through the outer portion OP of the photographic region PA, to be leveled with the overlap density of the projection data, at a time of the X-ray beam L to be detected by the X-ray sensor 12 being transmitted through the inner portion IP of the photographic region PA.

Therefore, an X-ray photography device 1 can be provided that is capable of improving the image quality in the entire photographic region PA.

Note that in the invention, the term "leveling control" is not intended to refer only to completely leveling the overlap density of the projection data at the outer portion OP of the imaging region PA with that at the inner portion IP, but is used as a concept inclusive of leveling the overlap density of the projection data more than the condition in the comparative example shown in FIG. 15, for example. In addition, the number of times for taking the projection data per unit time may be varied linearly, in a curved shape, or in incremental steps between at the outer portion OP and inner portion IP of the imaging region PA.

In addition, in the present embodiment, the controller 8 makes the X-ray sensor 12 detect the X-ray beam L transmitted through the object K, while swinging the X-ray source 11a and the X-ray sensor 12 around the object K and at the same time shifting a portion of the object K through which the X-ray beam L to be detected by the X-ray sensor 12 is transmitted. According to such a configuration, a halt and restart of a driven member such as X-ray sensor 12 can be reduced. As a result, a speed reduction due to the halt and restart of the driven member can be avoided from the beginning of the X-ray photography to the end thereof to allow for shortening an overall photographic time and for improving photographic efficiency. Further, acceleration and deceleration acting on the driven member can be reduced to cause an inertial force due to the acceleration and deceleration to be reduced, allowing for reducing vibration of the driven member due to the inertial force to improve durability of the driven member. That is, the X-ray sensor 12 having a relatively narrow-range detection area can be used to reduce the cost, and also photographic efficiency can be improved as well as vibration of the driven member such as X-ray sensor 12 can be reduced.

In the present embodiment, the X-ray source 11a and the X-ray sensor 12 are arranged to the arc motion arm 2 as a support member, and the arc motion arm 2 is rotatably supported about the arc motion central-axis C2 arranged in the swing arm 32 to allow the swing driver 3 to swing the X-ray source 11a and the X-ray sensor 12 arranged to the arc motion arm 2 around the object K via the swing arm 32. In addition, the arc motion arm 2 can be rotated by the shifter 5 as an arc motion driver to move the X-ray sensor 12 in an arc about the arc motion central-axis C2, allowing for shifting a portion of the object K through which the X-ray beam L is transmitted.

Second Embodiment

Figure 16:
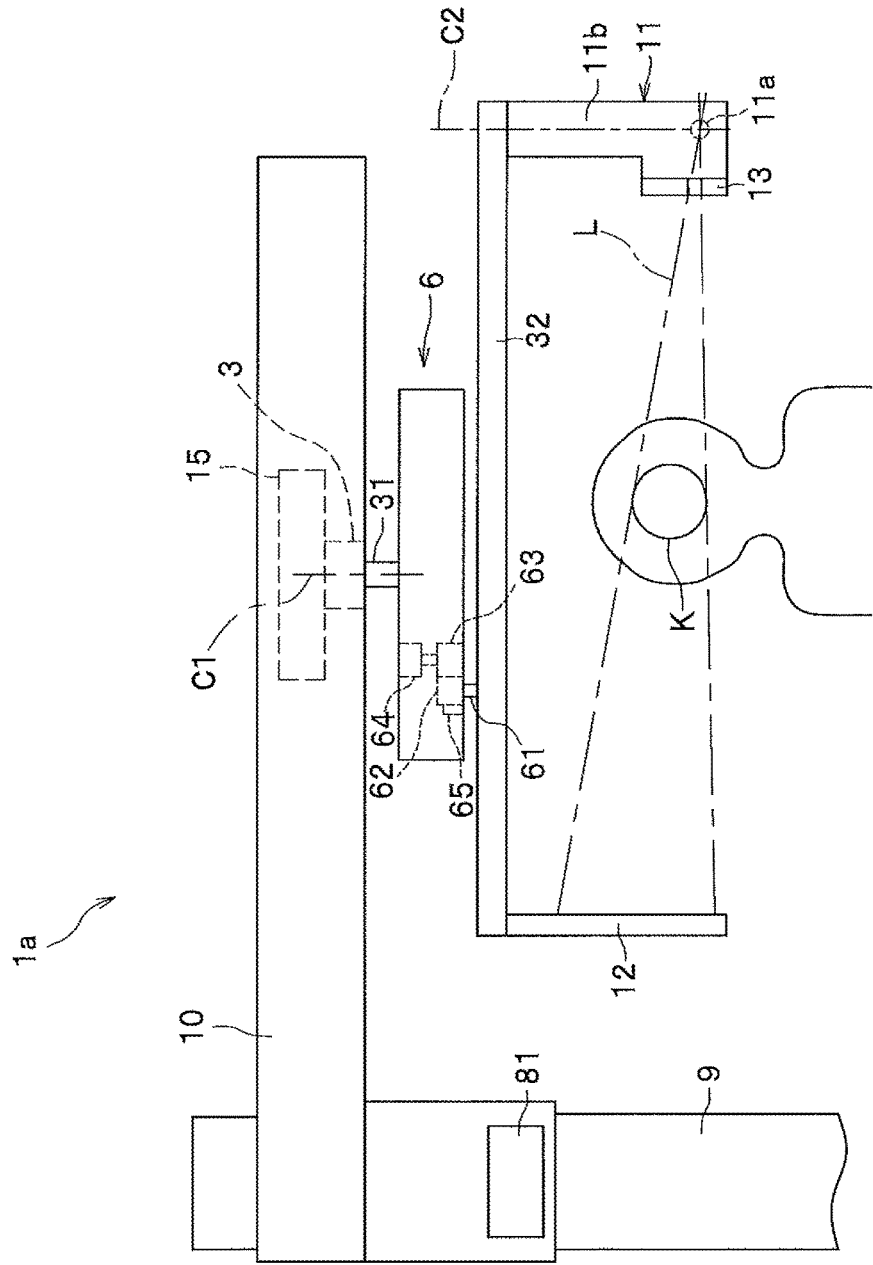
FIG. 16 is a side view schematically showing an overall configuration of an X-ray photography device according to a second embodiment of the invention.
Figure 17:
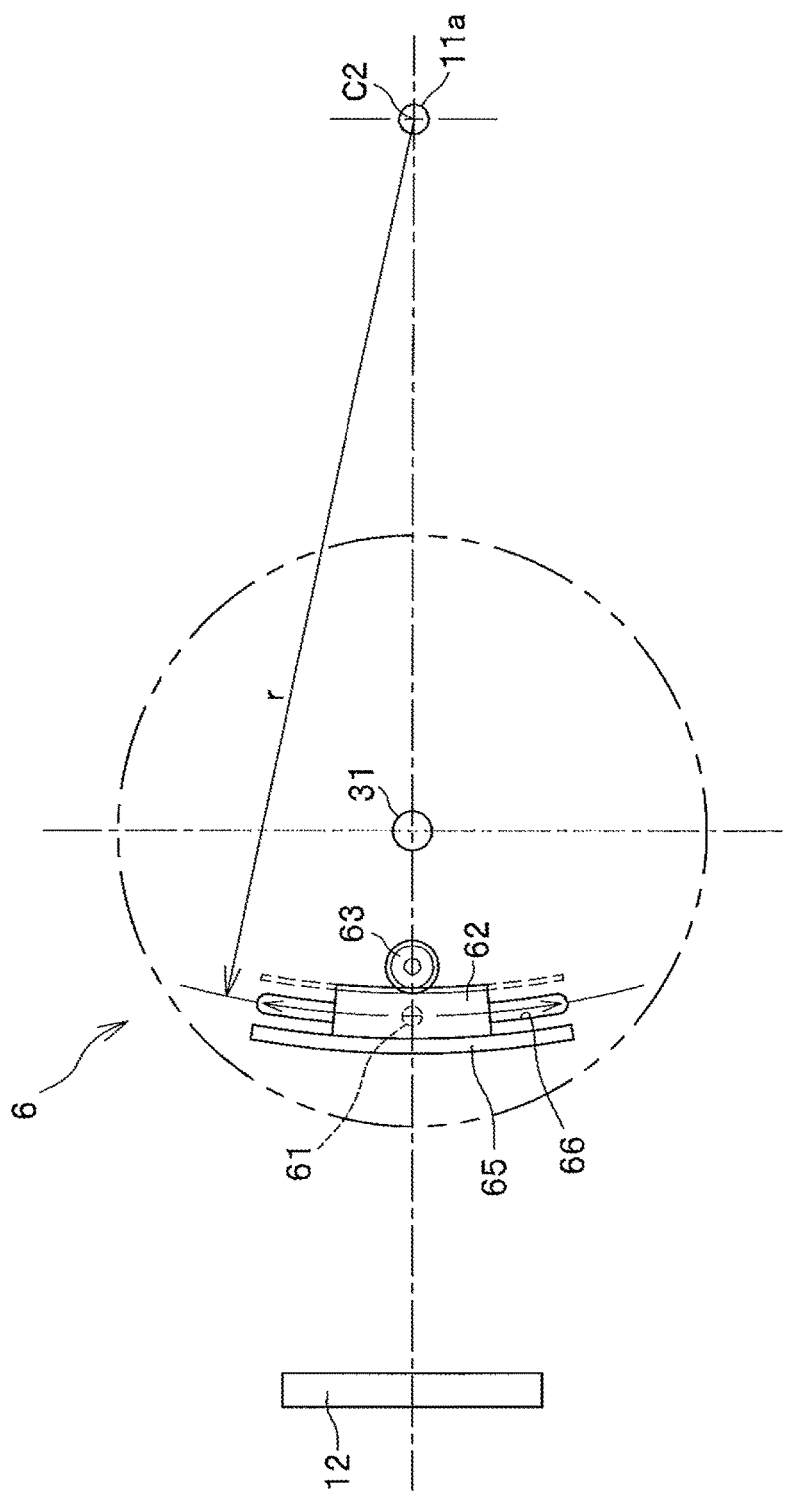
FIG. 17 is a plan view schematically showing a shifter and its surroundings according to the second embodiment.
Figure 18:
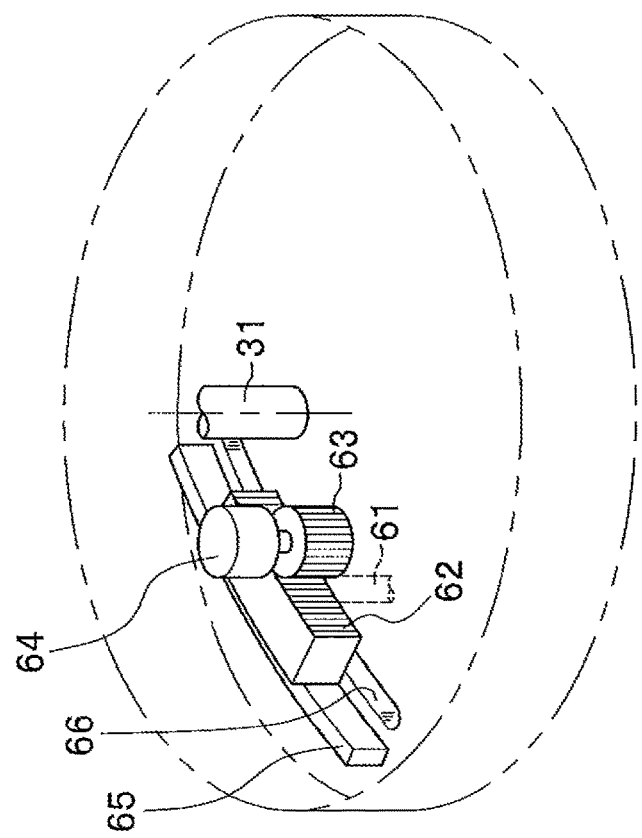
FIG. 18 is a perspective view schematically showing the shifter and its surroundings according to the second embodiment.

FIG. 16 is a side view schematically showing an overall configuration of an X-ray photography device 1a according to a second embodiment of the invention. FIG. 17 is a plan view schematically showing a shifter and its surroundings according to the second embodiment. FIG. 18 is a perspective view schematically showing the shifter and its surroundings according to the second embodiment. For the X-ray photography device 1a according to the second embodiment, a description will be given of those points which are different from the X-ray photography device 1 according to the first embodiment as described above.

As shown in FIG. 16, in the X-ray photography device 1a according to the second embodiment of the invention, a shifter 6 is different from the shifter 5 of the first embodiment on the point that the shifter 6 is a circumferentially-moving-swing-center-position mechanism which moves a swing center of the swing arm 32 as a support member in a circumferential direction of a circle about a point on a line connecting the X-ray source 11a with the X-ray sensor 12, here, about a point on the arc motion central-axis C2 that is a vertical axis running through the X-ray source 11a. Note that in the second embodiment, the horizontally-moving-swing-center-position mechanism 4 as in the first embodiment is omitted, but may be included in the configuration. The swing shaft 31 is fixed on the shifter 6, and the shifter 6 has a connecting shaft 61 which is fixed on the upper surface of the swing arm 32. The shifter 6 has a function of moving the connecting shaft 61 in an arc about the arc motion central-axis C2, resulting in moving the swing center position of the swing arm 32 in an arc about the arc motion central-axis C2. Here, the swing center position of the swing arm 32 is equal to the intersection on the swing arm 32 with the arm swing central-axis C1.

As shown in FIGS. 16 to 18, the shifter 6 includes: a sliding gear 62 that has an arc shape and seats the connecting shaft 61; a pinion gear 63 that is meshed with the sliding gear 62; a pinion-gear rotation driver 64 such as a servo motor that rotates the pinion gear 63; and a guide member 65 that guides a circumferential movement (arc motion) of the sliding gear 62. The sliding gear 62 is formed with inner teeth on the inner side in an arc about the arc motion central-axis C2. That is, in the shifter 6, the pinion-gear rotation driver 64 is driven to rotate the pinion gear 63 and then to move the sliding gear 62 through the gear force, thereby allowing the connecting shaft 61 to be shifted in the circumferential direction of a circle having a radius "r" (see FIG. 17) about the arc motion central-axis C2. Note that a reference numeral 66 in FIG. 17 or 18 shows a guide groove that guides the connecting shaft 61 moving around.

According to the second embodiment, the swing arm 32 as a support member, to which the X-ray source 11a and the X-ray sensor 12 is arranged, is swung by the swing driver 3 about a swing center position of the swing arm 32, and at the same time the swing center position of the swing arm 32 is moved in the circumferential direction about the arc motion central-axis C2 by the shifter 6 as a circumferentially-moving-swing-center-position mechanism. This causes the X-ray sensor 12 to be moved in an arc about the arc motion central-axis C2, to allow for shifting a portion of the object K through which the X-ray beam L is transmitted. Therefore, the second embodiment can also be used to achieve the same operational effects as the first embodiment described above.

Third Embodiment

Figure 19:
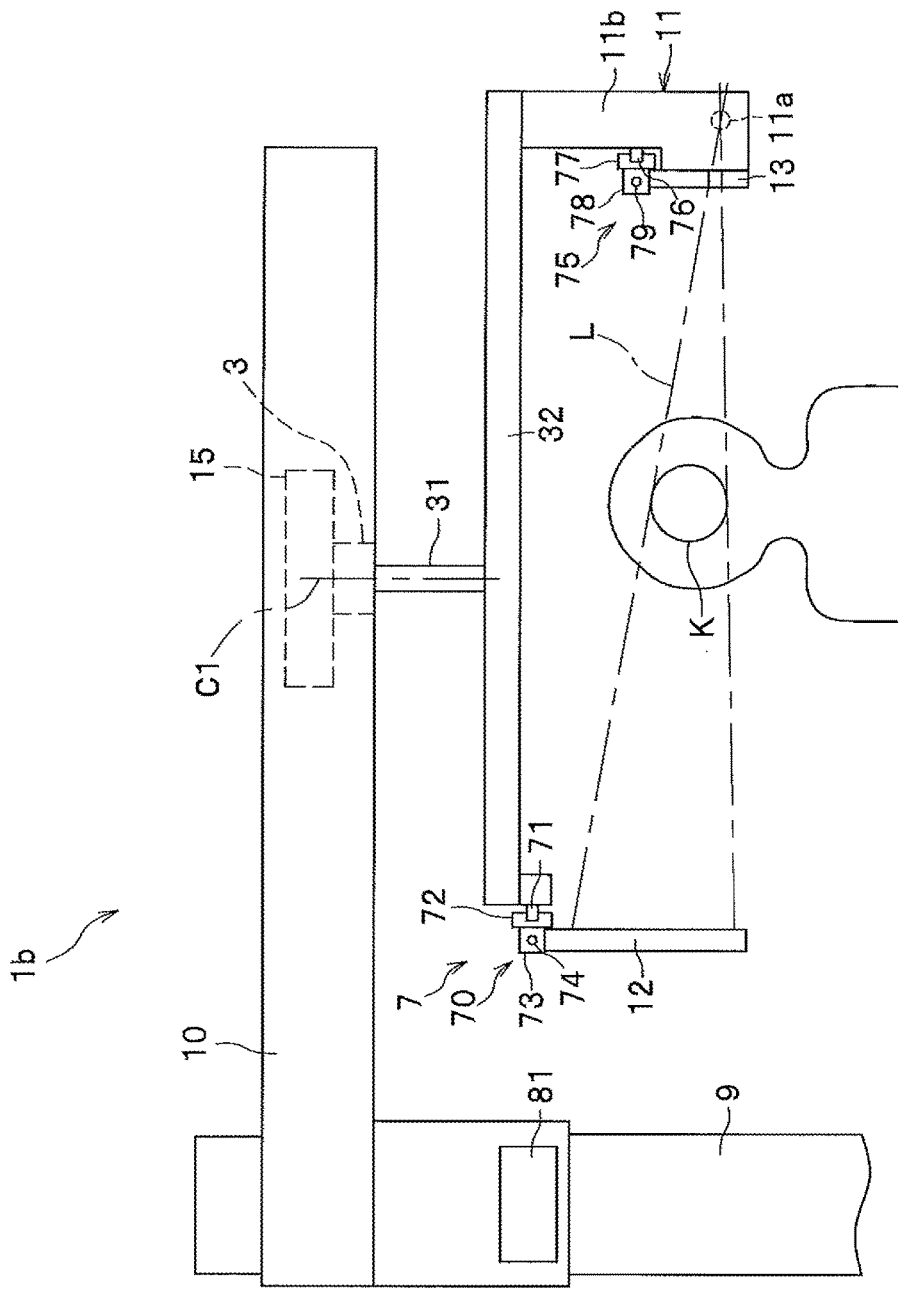
FIG. 19 is a side view schematically showing an overall configuration of an X-ray photography device according to a third embodiment of the invention.

FIG. 19 is a side view schematically showing an overall configuration of an X-ray photography device 1b according to a third embodiment of the invention. Hereinbelow, a description will be given of the X-ray photography device 1b according to the third embodiment on the point that differs from the X-ray photography device 1 according to the first embodiment described above.

As shown in FIG. 19, in the X-ray photography device 1b according to the third embodiment of the invention, a shifter 7 is different from the shifter 5 of the first embodiment on the point that the shifter 7 is arranged to the swing arm 32 as a support member to linearly move the X-ray sensor 12. Note that the horizontally-moving-swing-center-position mechanism 4 as in the first embodiment is omitted in the third embodiment, but may be included in the configuration. Note that the X-ray sensor 12 is moved in an arc about the arc motion central-axis C2 in the first and second embodiments described above, and the third embodiment falls into a case where the arc motion central-axis C2 (see FIGS. 1 and 16) is located at an extremely long distance from the object K.

The shifter 7 includes: a linear motion driver 70 that linearly moves the X-ray sensor 12; and a linear motion driver 75 that linearly moves the slit 13 for restricting the range of the X-ray beam L radiated from the X-ray source 11a. The linear motion driver 70 is arranged to the swing arm 32. The linear motion driver 75 is arranged via the support portion 11b to the swing arm 32, but may be arranged directly to the swing arm 32. The linear motion driver 70 includes: a guide rail 71 that is arranged along the direction to be linearly moved; a holder 72 that is mounted so as to be freely reciprocate along the guide rail 71; a nut portion 73 that is fixed to the holder 72; a male screw member 74 that is screwed to the nut portion 73; and a male screw member rotator (not shown) such as a servo motor that rotates the male screw member 74. Likewise, the linear motion driver 75 for linearly moving the slit 13 includes: a guide rail 76; a holder 77; a nut portion 78; a male screw member 79; and a male screw member rotator (not shown) such as a servo motor that rotates the male screw member 79. Then, the linear motion driver 70 and the linear motion driver 75 are controlled so as to be moved synchronously with each other.

According to the third embodiment, the X-ray sensor 12 can linearly be moved by the shifter 7 to shift a portion of the object K through which the X-ray beam L is transmitted. Therefore, the third embodiment can also be used to achieve the same operational effects as the first embodiment described above.

Fourth Embodiment

A fourth embodiment is one in which leveling control by the controller 8 for leveling the overlap density of the projection data is different from that in the first to third embodiments described above. As other configurative elements are the same as those in any of the first to third embodiments described above, they will be omitted.

A leveling control according to the fourth embodiment is a control that makes the speed (angular velocity) of swinging by the swing driver 3 the X-ray source 11a and the X-ray sensor 12 around the object K at a time of the X-ray beam L to be detected by the X-ray sensor 12 being transmitted through the outer portion OP of the photographic region PA, slower than the speed (angular velocity) of swinging by swing driver 3 the X-ray source 11a and the X-ray sensor 12 around the object K at a time of the X-ray beam L to be detected by the X-ray sensor 12 being transmitted through the inner portion IP of the photographic region PA. Note that the speed of swinging the X-ray source 11a and the X-ray sensor 12 around the object K may be varied linearly, in a curved shape, or in incremental steps between at the outer portion OP and inner portion IP of the photographic region PA.

According to the fourth embodiment, the speed (angular velocity) of swinging by the swing driver 3 the X-ray source 11a and the X-ray sensor 12 around the object K can be varied between at the outer portion OP and inner portion IP of the photographic region PA, to level the overlap density of the projection data in the outer portion OP and inner portion IP of the photographic region PA. Therefore, the fourth embodiment can also be used to achieve the same operational effects as the first to third embodiments described above.

Fifth Embodiment

A fifth embodiment is one in which leveling control by the controller 8 for leveling the overlap density of the projection data is different from that in the first to third embodiments described above. As other configurative elements are the same as those in any of the first to third embodiments described above, they will be omitted.

A leveling control according to the fifth embodiment is a control that makes the speed of shifting by the shifter 5 a portion of the object K through which the X-ray beam L is transmitted at a time of the X-ray beam L to be detected by the X-ray sensor 12 being transmitted through the outer portion OP of the photographic region PA, slower than the speed of shifting by the shifter 5 a portion of the object K through which the X-ray beam L is transmitted at a time of the X-ray beam L to be detected by the X-ray sensor 12 being transmitted through the inner portion IP of the photographic region PA. Here, the speed of swinging by the swing driver 3 the X-ray source 11a and the X-ray sensor 12 around the object K is constant. Also, the time interval of sampling the projection data is constant for the outer portion OP and inner portion IP of the photographic region PA. Note that the speed of shifting a portion of the object K through which the X-ray beam L is transmitted may be varied linearly, in a curved shape, or in incremental steps between at the outer portion OP and inner portion IP of the photographic region PA.

Figure 20:
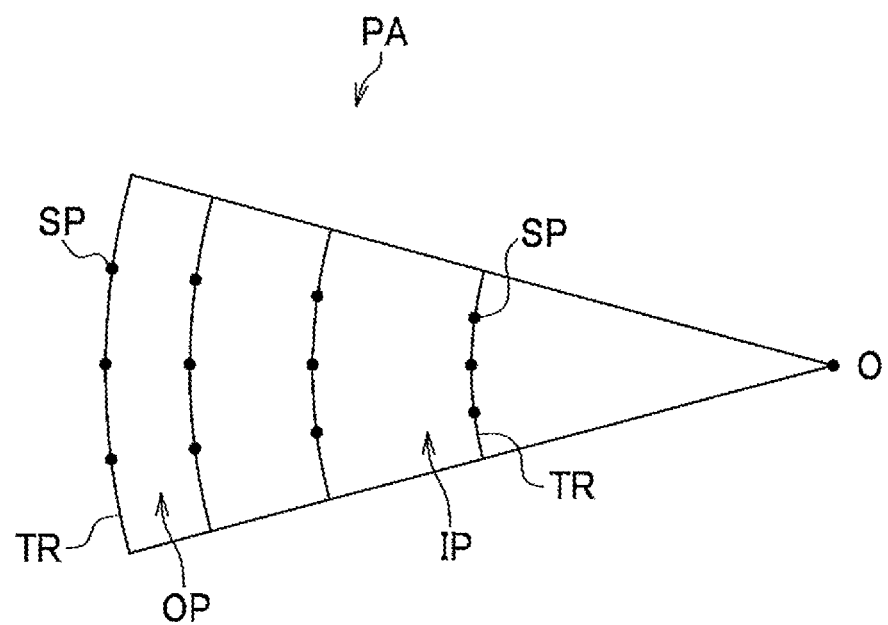
FIG. 20 is a partial plan view schematically showing a photographic region according to a fifth embodiment as viewed from a point in the direction along the central axis of the photographic region.

FIG. 20 is a partial plan view schematically showing a photographic region PA according to the fifth embodiment as viewed from a point in the direction along the central axis O of the photographic region PA. Note that the photography specification surface SF is not shown in FIG. 20. As the speed of shifting a portion of the object K through which the X-ray beam L is transmitted is decreased at the outer portion OP and increased at the inner portion IP, a distance between radially adjacent moving tracks TR of the photography specification points SP is dense at the outer portion OP and sparse at the inner portion IP, as shown in FIG. 20. This means that the number of the photography specification points SP per unit area in the plane shown in FIG. 20, i.e., the number of the photography specification surfaces SF, is made uniform.

According to the fifth embodiment, the speed of shifting by the shifter 5 a portion of the object K through which the X-ray beam L is transmitted can be varied between at the outer portion OP and inner portion IP of the photographic region PA, to level the overlap density of the projection data at the outer portion OP and inner portion IP of the photographic region PA. Therefore, the fifth embodiment can also be used to achieve the same operational effects as the first to third embodiments described above. In addition, what is moved by the shifter 5 is the X-ray sensor 12, which has small mass, or the like to facilitate controlling the shifting speed.

Hereinabove, the invention has been described based on the embodiments, but the invention is not limited to the configurations described in the embodiments, and the configuration can be modified as appropriate within the scope of the spirit of the invention, inclusive of combining or selecting the configurations described in the embodiments as appropriate.

For example, the invention is also applicable to a case where a control is made so that detecting by the X-ray sensor 12 the X-ray beam L that has transmitted the object K, while swinging the X-ray source 11a and the X-ray sensor 12 around the object K, and shifting a portion of the object K through which the X-ray beam L to be detected by the X-ray sensor 12 is transmitted are alternately repeated. In addition, the invention is also applicable to a case where a control is made so that detecting by the X-ray sensor 12 the X-ray beam L that has transmitted the object K, while shifting a portion of the object K through which the X-ray beam L is transmitted, and swinging the X-ray source 11a and the X-ray sensor 12 around the object K are alternately repeated.

In addition, the size of the shift amount S can be set as appropriate depending on such as necessary resolution of the CT image. For example, the shift amount S may be set so that there is a gap between a portion through which the X-ray beam L has been transmitted before one rotation of the arc motion arm 2 and a portion through which the X-ray beam L radiated from the same position of the rotation as above is transmitted after the one rotation and which is adjacent to the preceding portion, or may be set so that above-mentioned portions partially overlap with each other. Alternatively, such a setting can be made in which a shift amount S of the X-ray sensor 12 being shifted while the arc motion arm 2 makes such as a half rotation is substantially equal to the width of the X-ray sensor 12 (effective width) W.

Further, in the embodiments described above, the number of times for swinging the arc motion arm 2 is 5 times per every X-ray photography, but the number may be set as appropriate through the operation panel 81.

Furthermore, the shifters 5 to 7 are exemplary and are not limited to the configurations in the first to third embodiments as described above. For example, in the second embodiment, the X-ray source 11a may be configured so as to be moved in an arc around the X-ray sensor 12. Additionally, in the shifter 7 according to the third embodiment, a straight rack may be employed to configure a linear motion driver.

Moreover, in the first and second embodiments, the arc motion central-axis C2 is set to an axis vertically running through the X-ray source 11a, but is not limited thereto and can be set to an axis vertically running through a point on a line connecting the object K with the X-ray sensor 12. Additionally, the embodiments are each configured to arrange the slit 13 for restricting the range of the X-ray beam L, but is not limited thereto and the invention can be embodied without arranging the slit 13.

Still moreover, in the embodiments as described above, the X-ray photography process (step S1) is completed before the CT image generating process (step S2) is executed, but the invention is not limited thereto and the CT image generation may be executed, in the middle of the X-ray photography process, sequentially from a region for which image reconstruction has become ready. In this way, the overall CT photography operation time can further be reduced.

Still moreover, the X-ray photography device may be used in any medical practices other than a dental practice. Additionally, an object to be photographed may be a matter other than a human, and then the X-ray photography device may be used for inspecting a matter.

The invention claimed is:

1. An X-ray photography device comprising:
   an X-ray source that irradiates an object with an X-ray beam;
   an X-ray imager that detects the X-ray beam transmitted through the object;
   a support member that supports the X-ray source and the X-ray imager;
   a swing driver that rotates the support member to swing the X-ray source and the X-ray imager around the object;
   a shifter that shifts a portion of the object through which the X-ray beam to be detected by the X-ray imager is transmitted; and
   a controller that controls operation of the swing driver and the shifter,
   wherein assuming that a cross section obtained by cutting the X-ray beam at a time of taking projection data from the X-ray beam detected by the X-ray imager, with a plane, which is perpendicular to the central axis of the X-ray beam and runs through the central axis of a photographic region, is defined as a photography specification surface and the number of the photography specification surface per unit area in a plane, as the photographic region is viewed from a point in the direction along the central axis of the photographic region, is defined as overlap density of the projection data, the controller executes a leveling control which levels the overlap density of the projection data between at an outer portion and inner portion of the photographic region.

2. The X-ray photography device according to claim 1, wherein the controller operates the swing driver for rotating the support member to swing the X-ray source and the X-ray imager around the object, and at the same time operates the shifter to shift a portion of the object through which the X-ray beam to be detected by the X-ray imager is transmitted, to make the X-ray imager detect the X-ray beam transmitted through the object.

3. The X-ray photography device according to claim 1, wherein the leveling control makes a speed of shifting by the shifter a portion of the object through which the X-ray beam is transmitted at a time of the X-ray beam to be detected by the X-ray imager being transmitted through the outer portion of the photographic region, slower than a speed of shifting by the shifter the portion of the object through which the X-ray beam is transmitted at a time of the X-ray beam to be detected by the X-ray imager being transmitted through the inner portion of the photographic region.

4. The X-ray photography device according to claim 1, wherein the leveling control makes the number of times for taking the projection data per unit time at a time of the X-ray beam to be detected by the X-ray imager being transmitted through the outer portion of the photographic region, larger than the number of times for taking the projection data per unit time at a time of the X-ray beam to be detected by the X-ray imager being transmitted through the inner portion of the photographic region.

5. The X-ray photography device according to claim 1, wherein the leveling control makes a speed of swinging by the swing driver the X-ray source and the X-ray imager around the object at a time of the X-ray beam to be detected by the X-ray imager being transmitted through the outer portion of the photographic region, slower than a speed of swinging by the swing driver the X-ray source and the X-ray imager around the object at a time of the X-ray beam to be detected by the X-ray imager being transmitted through the inner portion of the photographic region.

6. The X-ray photography device according to claim 2, wherein the leveling control makes a speed of shifting by the shifter a portion of the object through which the X-ray beam is transmitted at a time of the X-ray beam to be detected by the X-ray imager being transmitted through the outer portion of the photographic region, slower than a speed of shifting by the shifter the portion of the object through which the X-ray beam is transmitted at a time of the X-ray beam to be detected by the X-ray imager being transmitted through the inner portion of the photographic region.

7. The X-ray photography device according to claim 2, wherein the leveling control makes the number of times for taking the projection data per unit time at a time of the X-ray beam to be detected by the X-ray imager being transmitted through the outer portion of the photographic region, larger than the number of times for taking the projection data per unit time at a time of the X-ray beam to be detected by the X-ray imager being transmitted through the inner portion of the photographic region.

8. The X-ray photography device according to claim 2, wherein the leveling control makes a speed of swinging by the swing driver the X-ray source and the X-ray imager around the object at a time of the X-ray beam to be detected by the X-ray imager being transmitted through the outer portion of the photographic region, slower than a speed of swinging by the swing driver the X-ray source and the X-ray imager around the object at a time of the X-ray beam to be detected by the X-ray imager being transmitted through the inner portion of the photographic region.

\* \* \* \* \*